United States Patent [19]
Farmer et al.

[11] Patent Number: 6,005,007
[45] Date of Patent: Dec. 21, 1999

[54] RETINOIDS, METHODS FOR THEIR PRODUCTION AND USE

[76] Inventors: Luc J. Farmer; Lin Zhi, both of Ligand Pharmaceuticals Incorporated, 9393 Towne Centre Dr., San Diego, Calif. 92121

[21] Appl. No.: 08/896,881

[22] Filed: Jul. 18, 1997

[51] Int. Cl.$^6$ .......................... A61K 31/19; C07C 63/36; C07D 215/12; C07D 279/16
[52] U.S. Cl. .................. 514/569; 514/224.2; 514/230.5; 514/255; 514/311; 514/432; 514/434; 514/452; 514/456; 544/51; 544/105; 544/353; 546/174; 549/15; 549/23; 549/362; 549/407; 562/490
[58] Field of Search ............................... 514/569; 562/490

[56] References Cited

FOREIGN PATENT DOCUMENTS

97/12853  4/1997  WIPO .

*Primary Examiner*—Jose' G. Dees
*Assistant Examiner*—Barbara Badio
*Attorney, Agent, or Firm*—J. Scott Elmer; William L. Respess

[57] ABSTRACT

Dienoic retinoids having activity for retinoid X receptors or are panagonists on retinoic acid receptors and retinoid X receptors are provided. Also provided are pharmaceutical compositions incorporating such compounds and methods for their therapeutic use.

34 Claims, No Drawings

RETINOIDS, METHODS FOR THEIR PRODUCTION AND USE

FIELD OF THE INVENTION

The present invention relates to retinoid compounds having activity for retinoic acid receptors and/or retinoid X receptors, and to methods for the production and therapeutic use of such compounds.

BACKGROUND OF THE INVENTION

The vitamin A metabolite, retinoic acid, has long been recognized to induce a broad spectrum of biological effects. In addition, a variety of structural analogues of retinoic acid have been synthesized that also have been found to be bioactive. Some, such as Retin-A® and Accutane®, have found utility as therapeutic agents for the treatment of various pathological conditions. In addition, synthetic retinoids have been found to mimic many of the pharmacological actions of retinoic acid.

Medical professionals have become very interested in the therapeutic applications of retinoids. Among their uses approved by the FDA is the treatment of severe forms of acne and psoriasis. A large body of evidence also exists that these compounds can be used to arrest and, to an extent, reverse the effects of skin damage arising from prolonged exposure to the sun. Other evidence exists that these compounds may be useful in the treatment and prevention of a variety of cancerous and pre-cancerous conditions, such as melanoma, cervical cancer, some forms of leukemia, oral leukoplakia and basal and squamous cell carcinomas. Retinoids have also shown an ability to be efficacious in treating and preventing diseases of the eye, cardiovascular system, immune system, skin, respiratory and digestive tracts, and as agents to facilitate wound healing and modulate programmed cell death (apoptosis).

Major insight into the molecular mechanism of retinoic acid signal transduction was gained in 1988, when a member of the steroid/thyroid hormone intracellular receptor superfamily was shown to transduce a retinoic acid signal. Evans, *Science,* 240:889–95 (1988); Giguere et al., *Nature,* 330:624–29 (1987); Petkovich et al., *Nature,* 330: 444–50 (1987). It is now known that retinoids regulate the activity of two distinct intracellular receptor subfamilies; the Retinoic Acid Receptors (RARs) and the Retinoid X Receptors (RXRs), including their isoforms, RARα, β, γ and RXRα, β, γ. In this regard, an endogenous low-molecular-weight ligand which modulates the transcriptional activity of the RARs is all-trans-retinoic acid (ATRA), while an endogenous ligand for the RXRs is 9-cis retinoic acid (9-cis). Heyman et al., *Cell,* 68:397–406 (1992) and Levin et al. *Nature,* 355:359–61 (1992).

Although both the RARs and RXRs respond to ATRA in vivo, due to the in vivo conversion of some of the ATRA to 9-cis, the receptors differ in several important aspects. First, the RARs and RXRs are significantly divergent in primary structure (e.g., the ligand binding domains of RARα and RXRα have only 27% amino acid identity). These structural differences are reflected in the different relative degrees of responsiveness of RARs and RXRs to various vitamin A metabolites and synthetic retinoids. In addition, distinctly different patterns of tissue distribution are seen for RARs and RXRs. For example, in contrast to the RARs, which are not expressed at high levels in the visceral tissues, RXRα MRNA has been shown to be most abundant in the liver, kidney, lung, muscle and intestine. Finally, the RARs and RXRs have different target gene specificity. For example, response elements have recently been identified in the cellular retinal binding protein type II (CRBPII) and Apolipoprotein AI genes which confer responsiveness to RXR, but not RAR. Furthermore, RAR has also been recently shown to repress RXR-mediated activation through the CRBPII RXR response element (Manglesdorf et al., *Cell,* 66:555–61 (1991)). These data indicate that two retinoic acid responsive pathways are not simply redundant, but instead manifest a complex interplay.

In view of the related, but clearly distinct, nature of these receptors, retinoids which are more selective for the RAR subfamily or the RXR subfamily would be of great value for selectively controlling processes mediated by one or more of the RAR or RXR isoforms, and would provide the capacity for independent control of the physiologic processes mediated by the RARs or RXRs. In addition, pan-agonist retinoids that activate one or more isoforms of both the RARs and RXRs would also be valuable for controlling processes mediated by both of these subfamilies of retinoid receptors. Furthermore, retinoids which preferentially affect one or more but not all of the receptor isoforms also offer the possibility of increased therapeutic efficacy and reduced side effect profiles when used for therapeutic applications.

Various polyene compounds have been disclosed to be useful in the treatment of inflammatory conditions, psoriasis, allergic reactions, and for use in sunscreens in cosmetic preparations. See e.g., U.S. Pat. Nos. 4,534,979 and 5,320,833 and Australian Patent Application No. 16511/95 . In addition, trienediolates of hexadienoic acids have proved useful in the synthesis of retinoic and nor-retinoic acids. See M. J. Aurell, et al., 49 *Tetrahedron,* 6089 (1993). Further, RXR active compounds have been disclosed by the Assignee and others. See, e.g., PCT US93/03944, US93/10166, US93/10094, US93/10204, US95/16842, US95/07390, US96/14876 and EP 0 718 285. Finally, Assignee has disclosed trienoic compounds with retinoid-like activity. See M. F. Boehm, et al., 39 Journal of Medicinal Chemistry, 2659 (1996) and PCT US95/16695 and US96/14876.

SUMMARY OF THE INVENTION

The present invention provides novel dienoic retinoid compounds that have selective activity as RXR agonists or pan-agonist activity on one or more of each of the RAR and RXR isoforms. The present invention also provides pharmaceutical compositions incorporating these novel dienoic compounds and methods for the therapeutic use of such compounds and pharmaceutical compositions.

These and various other advantages and features of novelty which characterize the invention are pointed out with particularity in the claims annexed hereto and forming a part hereof. However, for a better understanding of the invention, its advantages, and objects obtained by its use, reference should be had to the accompanying drawings and descriptive matter, in which there is illustrated and described preferred embodiments of the invention.

DEFINITIONS

In accordance with the present invention and as used herein, the following terms are defined with the following meanings, unless explicitly stated otherwise.

The term alkyl refers to straight-chain, branched-chain, cyclic structures, and combinations thereof.

The term aryl refers to an optionally substituted six-membered aromatic ring.

The term heteroaryl refers to an optionally substituted five-membered or six-membered heterocyclic ring containing one or two heteroatoms selected from the group consisting of oxygen, nitrogen and sulfur, and more preferably one heteroatom selected from the group consisting of oxygen, nitrogen and sulfur. It will also be understood that the terms 'aryl' and 'heteroaryl' also encompass bi- and tri-aryls, bi- and tri-heteroaryls and any combination of up to three rings including at least one aryl fused to at least one heteroaryl, e.g., biphenyl, naphtyl, anthracenyl, furyl, pyrralyl, pyrralidinyl, thienyl, pyridyl, piperidyl, indolyl and quinolyl.

The terms retinoid or retinoids refer to compound(s) that bind and/or activate one or more retinoid receptors, thereby affecting the transcriptional activity of a target gene to which the activated receptor and compound complex binds.

The term pan-agonist refers to a retinoid that activates at least one member of both the RAR subfamily (i.e., RARα, RARβ, or RARγ) and the RXR subfamily (i.e., RXRα, RXRβ, or RXRγ). Preferably such pan-agonist retinoids activate all members of both the RAR and RXR subfamilies of retinoid receptors.

DETAILED DESCRIPTION OF EMBODIMENTS OF THE INVENTION

In accordance with a first aspect of the present invention, we have developed dienoic retinoid compounds of the formula:

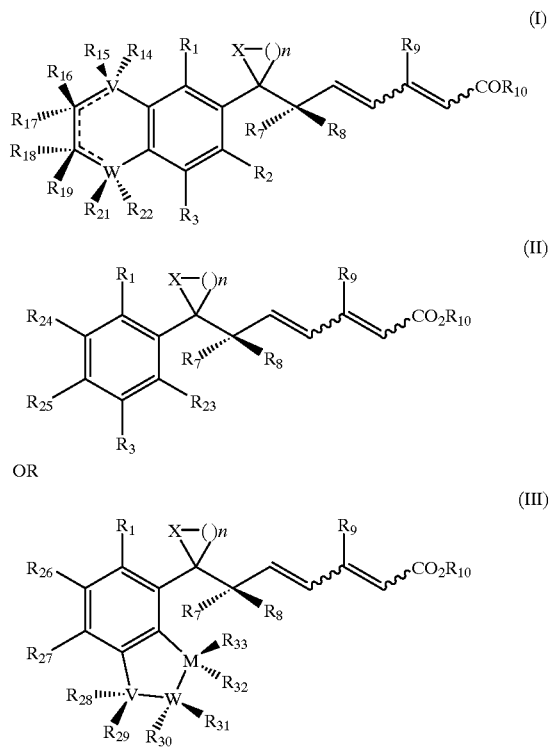

wherein
$R_1$ is hydrogen or a $C_1$–$C_{10}$ alkyl, F or $Or_4$, where $R_4$ has the definition given below;

$R_2$ is hydrogen, $CH_3$, $OCH_3$ or $NO_2$;

$R_3$ is hydrogen, F, a $C_1$–$C_{12}$ alkyl, $CF_3$, $NO_2$, $OR_4$ or $NR_5R_6$, where $R_4$ is hydrogen, a $C_1$–$C_6$ alkyl or $C_1$–$C_{15}$ arylalkyl, and where $R_5$ and $R_6$ each independently are hydrogen, a $C_1$–$C_6$ alkyl, $C_7$–$C_{15}$ arylalkyl, aryl, ortho-, meta-, or para-substituted hydroxyalkyl or taken together are a $C_3$–$C_6$ cycloalkyl, provided that $R_5$ must be a hydrogen when $R_6$ is aryl or hydroxyaryl;

$R_7$ and $R_8$ each independently are hydrogen or a $C_1$–$C_6$ alkyl;

$R_9$ is hydrogen or a $C_1$–$C_6$ alkyl or $CF_3$;

$R_{10}$ is $OR_{11}$ or $NR_{12}R_{13}$, where $R_{11}$ is hydrogen, a $C_1$–$C_6$ alkyl, with $R_{12}$ and $R_{13}$ each independently being hydrogen, a $C_1$–$C_6$ alkyl, aryl or ortho-, meta- and para-substituted hydroxy aryl;

$R_{14}$–$R_{15}$ each independently are hydrogen, a $C_1$–$C_{12}$ alkyl, $C_7$–$C_{15}$ arylalkyl or $CF_3$;

$R_{16}$–$R_{19}$ each independently are hydrogen, a $C_1$–$C_{12}$ alkyl, $C_7$–$C_{15}$ arylalkyl, $CF_3$, $OR_{20}$ or $NR_5R_6$, where $R_{20}$ is hydrogen, benzyl, a $C_1$–$C_{10}$ alkyl or a $C_1$–$C_{15}$ arylalkyl, and where $R_5$ and $R_6$ have the definitions given above, or $R_{16}$–$R_{19}$ taken together are keto or $R_{16}$ and $R_{17}$, $R_{18}$ and $R_{19}$, $R_{16}$ and $R_{19}$, $R_{17}$ and $R_{18}$ are epoxy or cyclopropyl;

$R_{21}$ and $R_{22}$ each independently are hydrogen, a $C_1$–$C_6$ alkyl or a $C_7$–$C_{15}$ arylalkyl;

$R_{23}$ is hydrogen, $NO_2$, a $C_1$–$C_6$ alkyl or $OR_{20}$, where $R_{20}$ has the definition given above;

$R_{24}$–$R_{27}$ each independently are hydrogen, a $C_1$–$C_{12}$ alkyl, $C_7$–$C_{15}$ arylalkyl, $CF_3$, $OR_{20}$ or $NR_5R_6$, where $R_5$, $R_6$ and $R_{20}$ have the definitions given above;

$R_{28}$–$R_{33}$ each independently are hydrogen, a $C_1$–$C_{12}$ alkyl, $C_7$–$C_{15}$ arylalkyl or $CF_3$;

V, M and W independently represent C, O, S, N, SO or $SO_2$, provided, however, that when V or M or W are O, S, SO and $SO_2$, then $R_{14}$ and $R_{15}$ or $R_{16}$ and $R_{17}$ or $R_{18}$ and $R_{19}$ or $R_{21}$ and $R_{22}$ in structures I and III respectively do not exist, and further provided, that when V or M or W is N, then one each of $R_{14}$ and $R_{15}$ or $R_{16}$ and $R_{17}$ or $R_{18}$ and $R_{19}$ or $R_{21}$ and $R_{22}$ in structures I and III respectively, do not exist;

X represents C, O, N or $CF_2$;

n=1, 2, 3 or 4;

the dotted lines in structures I and III represent optional double bonds; and the wavy lines represent olefin bonds that are either in the cis (Z) or trans (E) configuration, provided, however, that the double bonds cannot be contiguous, and further provided that when such optional double bonds exist then the substitution patterns around such bonds cannot violate double bond valency.

Preferably,
$R_1$ is hydrogen, $CH_3$ or $OCH_3$;
$R_2$ is hydrogen, $CH_3$ or $OCH_3$;
$R_3$ is hydrogen, F, a $C_1$–$C_2$ alkyl, $NO_2$ or $OR_4$, where $R_4$ is a $C_1$–$C_3$ alkyl;
$R_7$ and $R_8$ each independently are hydrogen or a $C_1$–$C_2$ alkyl;
$R_9$ is a $C_1$–$C_2$ alkyl or $CF_3$;
$R_{10}$ is $OR_{11}$, where $R_{11}$ is hydrogen, a $C_1$–$C_2$ alkyl or Na or Ca;
$R_{14}$–$R_{22}$ each independently are hydrogen or a $C_1$–$C_2$ alkyl;
$R_{23}$ is hydrogen or a $C_1$–$C_3$ alkyl;
$R_{24}$–$R_{33}$ each independently are hydrogen or a $C_1$–$C_2$ alkyl;
V, M and W independently represent C, S or N;
X represents C or $CF_2$;
n=1, 2 or 3;
the dotted lines in structures I and III represent optional double bonds; and
the wavy lines represent olefin bonds that are either in the cis (Z) or trans (E) configuration, provided, however, that the double bonds cannot be contiguous, and further provided that when such optional double bonds exist then the substitution patterns around such bonds cannot violate double bond valency.

In a first preferred aspect, the compounds of structure I are retinoid compounds of the formula:

[Chemical structure I with substituents $R_1$, $R_2$, $R_3$, $R_7$, $R_8$, $R_9$, $R_{14}$, $R_{15}$, $R_{16}$, $R_{17}$, $R_{18}$, $R_{19}$, $R_{21}$, $R_{22}$, $COR_{10}$, $X$–$()_n$, V, W]

wherein, $R_1$ and $R_3$ each independently are hydrogen or a $C_1$–$C_{10}$ alkyl, F or $OR_4$, where $R_4$ has the definition given above;

$R_2$ is hydrogen, $NO_2$, $CH_3$ or $OCH_3$;

$R_7$ and $R_8$ each independently are hydrogen or a $C_1$–$C_6$ alkyl;

$R_9$ is hydrogen or a $C_1$–$C_6$ alkyl or $CF_3$;

$R_{10}$ is $OR_{11}$ or $NR_{12}R_{13}$, where $R_{11}$ is hydrogen, a $C_1$–$C_6$ alkyl, and with $R_{12}$ and $R_{13}$ each independently being hydrogen, a $C_1$–$C_6$ alkyl, aryl or ortho-, meta- and para-substituted hydroxy aryl;

$R_{14}$, $R_{15}$, $R_{21}$ and $R_{22}$ each independently are hydrogen, a $C_1$–$C_6$ alkyl or a $C_7$–$C_{15}$ arylalkyl;

$R_{16}$ through $R_{19}$ each independently are hydrogen, a $C_1$–$C_2$ alkyl or $OR_{23}$, where $R_{23}$ is hydrogen or a $C_1$–$C_{10}$ alkyl, or $R_{16}$–$R_{19}$ taken together are keto or $R_{16}$ and $R_{17}$, $R_{18}$ and $R_{19}$, $R_{16}$ and $R_{19}$, $R_{17}$ and $R_{18}$ are epoxy or cyclopropyl;

V and W independently represent C, O, S, N, SO or $SO_2$, provided, however, that when V or W are O, S, SO and $SO_2$, then either $R_{14}$ and $R_{15}$ or $R_{21}$ and $R_{22}$ respectively do not exist, and further provided, that when V or W is N, then one each of $R_{14}$ and $R_{15}$ or $R_{21}$ and $R_{22}$ respectively, do not exist;

X represents C, O, N or $CF_2$;

n=1, 2, 3 or 4;

the dotted lines in structures I and III represent optional double bonds; and the wavy lines represent olefin bonds that are either in the cis (Z) or trans (E) configuration, provided, however, that the double bonds cannot be contiguous, and further provided that when such optional double bonds exist then the substitution patterns around such bonds cannot violate double bond valency.

In a second preferred aspect, the retinoid compounds of structure II are compounds of the formula:

[Chemical structure II with substituents $R_1$, $R_3$, $R_7$, $R_8$, $R_9$, $R_{23}$, $R_{24}$, $R_{25}$, $CO_2R_{10}$, $X$–$()_n$]

wherein, $R_1$ is hydrogen or a $C_1$–$C_{10}$ alkyl;

$R_3$ and $R_{24}$ each independently are hydrogen, a $C_1$–$C_6$ alkyl, branched alkyl, $CF_3$ or $NR_{24}R_{25}$, where $R_{24}$ and $R_{25}$ are $C_1$–$C_4$ alkyls;

$R_7$ and $R_8$ are hydrogen or a $C_1$–$C_6$ alkyl;

$R_9$ is a hydrogen or a $C_1$–$C_6$ alkyl or $CF_3$;

$R_{10}$ is $OR_{11}$ or $NR_{12}R_{13}$, where $R_{11}$ is hydrogen, a $C_1$–$C_6$ alkyl, and with $R_{12}$ and $R_{13}$ each independently being hydrogen, a $C_1$–$C_6$ alkyl, aryl or ortho-, meta- and para-substituted hydroxy aryl;

$R_{23}$ is hydrogen, $NO_2$, a $C_1$–$C_6$ alkyl or $OR_{20}$, where $R_{20}$ has the definition given above;

$R_{25}$ is hydrogen, $C_1$–$C_8$ alkyl and $OR_{26}$ with $R_{26}$ being a $C_1$–$C_7$ alkyl or benzyl;

X represents C, O, N of $CF_2$;

n=1, 2, 3 or 4; and the wavy lines represent olefin bonds that are either in the cis (Z) or trans (E) configuration, provided, however, that the double bonds cannot be contiguous, and further provided that when such optional double bonds exist then the substitution patterns around such bonds cannot violate double bond valency.

In a third preferred aspect, the retinoid compounds of structure III are compounds of the formula:

[Chemical structure III with substituents $R_1$, $R_7$, $R_8$, $R_9$, $R_{26}$, $R_{27}$, $R_{28}$, $R_{29}$, $R_{30}$, $R_{31}$, $R_{32}$, $R_{33}$, $CO_2R_{10}$, $X$–$()_n$, M, V, W]

wherein, $R_1$ is hydrogen;

$R_{26}$–$R_{27}$ each independently are hydrogen, a $C_1$–$C_{12}$ alkyl, $C_7$–$C_{15}$ arylalkyl, $CF_3$, $OR_{20}$ or $NR_5R_6$, where $R_5$, $R_6$ and $R_{20}$ have the definitions given above;

$R_{28}$–$R_{33}$ each independently are hydrogen, a $C_1$–$C_{12}$ alkyl, $C_7$–$C_{15}$ arylalkyl or $CF_3$;

$R_7$ and $R_8$ each independently are hydrogen or a $C_1$–$C_6$ alkyl;

$R_9$ is a hydrogen or a $C_1$–$C_6$ alkyl or $CF_3$;

$R_{10}$ is $OR_{11}$ or $NR_{12}R_{13}$, where $R_{11}$ is hydrogen, a $C_1$–$C_6$ alkyl, and with $R_{12}$ and $R_{13}$ each independently being hydrogen, a $C_1$–$C_6$ alkyl, aryl or ortho-, meta- and para-substituted hydroxyaryl;

M, W and V each independently represent C, O or N;

X represents C, O, N or $CF_2$;

n=1, 2, 3 or 4;

the dotted lines represent optional double bonds; and the wavy lines represent olefin bonds that are either in the cis (Z) or trans (E) configuration, provided, however, that the double bonds cannot be contiguous, and further provided that when such optional double bonds exist then the substitution patterns around such bonds cannot violate double bond valency.

The compounds of the present invention also include all pharmaceutically acceptable salts, as well as esters and amides. Preferably, such salts, esters and anides, will be formed at the $R_{10}$ position. As used in this disclosure, pharmaceutically acceptable salts include, but are not limited to: pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl)aminomethane. Additional pharmaceutically acceptable salts are known to those skilled in the art.

The compounds of the present invention are particularly useful in the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin pigmentation agents and to treat and reverse the effects of age and photo damage to the skin. The compounds are also useful for the prevention and treatment of cancerous and pre-cancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of restenosis and as an agent to increase the level of circulating tissue plasminogen activator (TPA). Other uses for the compounds of the present invention include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and Amyotrophic Lateral Sclerosis (ALS), improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis. It will also be understood by those skilled in the art that the retinoid compounds of the present invention will prove useful in any therapy in which retinoids, including RAR selective retinoids, RXR selective retinoids, and pan-agonist retinoids will find application.

Furthermore, it will be understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative retinoids of the present invention include, without limitation, (2E, 4E)-6-[1-(5,5,8,8-Tetramethyl-5,6,7,8-tetrahydronaphtha-len-2-yl) cyclopropanyl]-3-methyl hexadienoic acid (Compound 101); (2E, 4E)-6-[(3,5,5,8,8-Pentamethyl-5,6,7,8-tetrahy-dronaphthalen-2-yl) cyclopropan-1-yl]-3-methyl hexadienoic acid (Compound 102); (2E, 4E)-6-[(5,5,8,8-Tetramethyl-3-methoxy-5,6,7,8-tetrahydronaphtha-len-2-yl) cyclopropan-1-yl]-3-methyl hexadienoic acid (Compound 103); (2E, 4E)-6-[(5,5,8,8-Tetramethyl-3-ethoxy-5,6,7,8-tetrahydronaphthalen-2-yl) cyclopropan-1-yl]-3-methyl hexadienoic acid (Compound 104); (2E, 4E)-6-[(3,5-di-t-butyl phenyl) cyclopropan-1-yl]-3-methyl hexadienoic acid (Compound 105); (2E, 4E)-6-[(3,4-diethyl phenyl) cyclopropan-1-yl]-methyl hexadi- enoic acid (Compound 106); (2E, 4E)-6-[1-(6-t-butyl-1,1-dimethyl-indan-4-yl)-cyclopropyl]-3-methyl hexadienoic acid (Compound 107); and (2E, 4E)-6-[(5,5,8,8-Tetramethyl-5,6,7,8-tetrahydronaphtha-len-2-yl) cyclopentane-1-yl]-3-methyl hexadienoic acid (Compound 108).

The compounds of the present invention can be obtained by modification of the compounds disclosed or by a total synthesis approach, by techniques known to those skilled in the art. In this regard, the synthesis of the compounds of the present invention often follow established retinoid synthesis schemes and techniques as described in M. I. Dawson and W. H. Okamura, "Chemistry and Biology of Synthetic Retinoids", Chapters 3, 8, 14 and 16, CRC Press, Inc., Florida (1990); M. I. Dawson and P. D. Hobbs, *The Synthetic Chemistry of Retinoids*, In Chapter 2: "The Retinoids, Biology, Chemistry and Medicine", M. B. Sporn et al., Eds. (2nd ed.), Raven Press, New York, N.Y., pp. 5–178 (1994); R. S. H. Liu and A. E. Asato, "Photochemistry and Synthesis of Stereoisomers of Vitamin A," 40 *Tetrahedron*, 1931 (1984); 43 *Cancer Res.*, 5268 (1983); 15 *Eur. J. Med. Chem.*, 9 (1980); U.S. Pat. Nos. 4,326,055 and 4,578,498, and PCT patent application PCT US96/14876 the disclosures of which are herein incorporated by reference. The sequence of steps of the general schemes of synthesizing the compounds of the present invention are shown below. In addition, more detailed and illustrative synthetic schemes for specific compounds of the present invention will be found in the Examples included herein.

SCHEME I: Synthesis of Compounds of Structure (I):

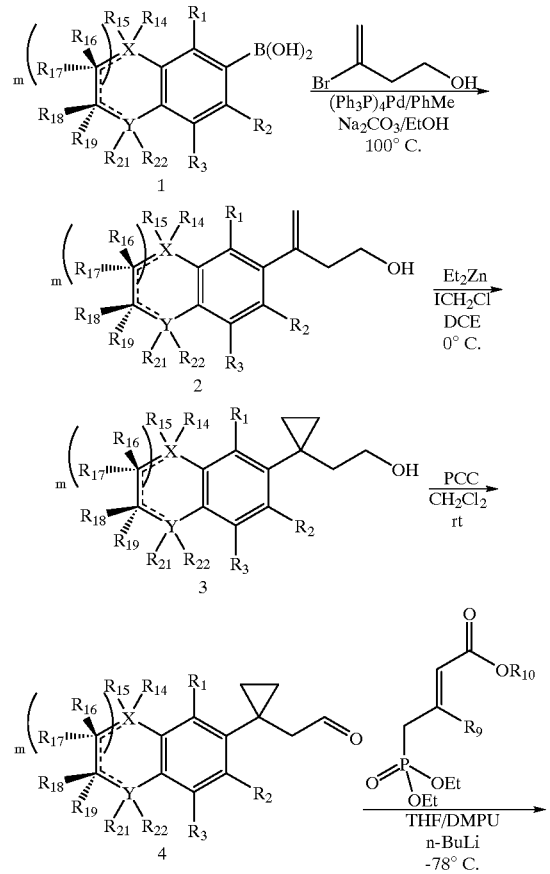

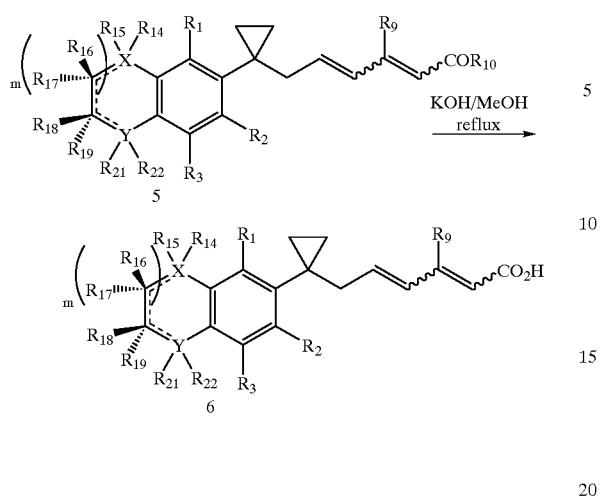

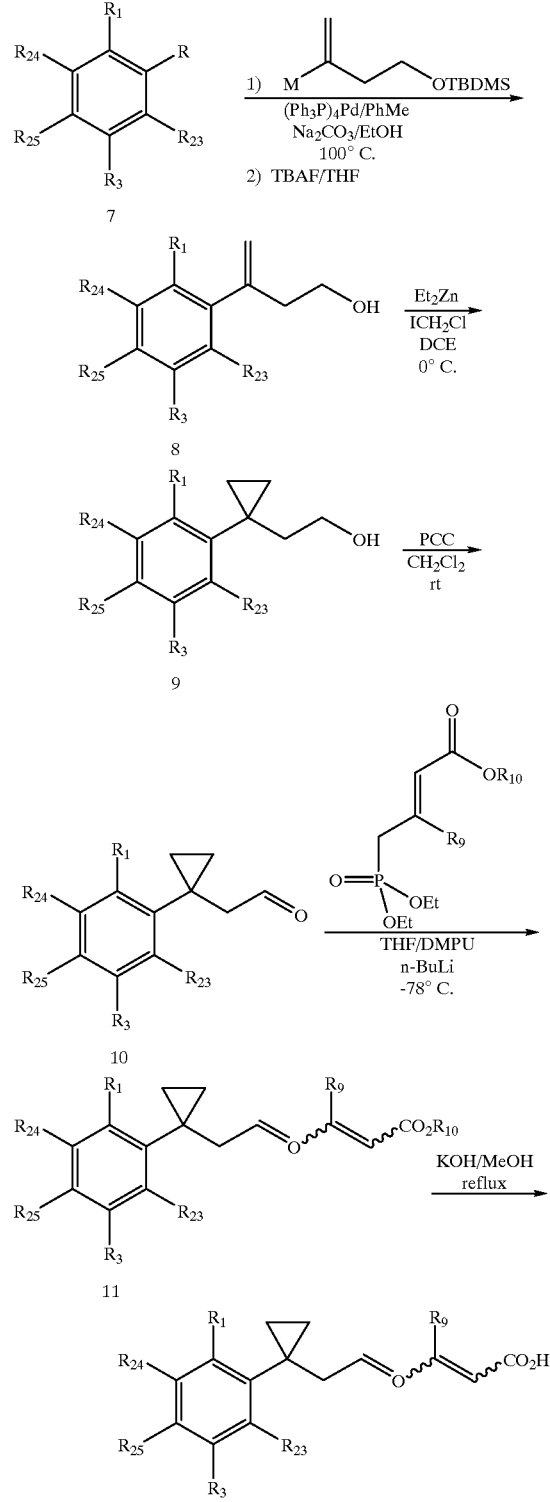

Scheme II: Synthesis of Compounds of Structure (II):

The bicyclic derivatives of the present invention, that is, compounds of general structures 6, may be prepared in accordance with Scheme I. Halogen-metal exchange of an appropriately substituted tetrahydrotetramethylnaphthalene such as 2-bromo-5,5,8,8-tetramethyl-5,6,7,8-tetrahydronaphthalen with a base, such as n-BuLi, followed by treatment with trimethyl borate and acidification with aqueous 10% hydrochloric acid provides the boronic acid precursor 1. The dienoic acid side chain precursor was introduced by the Suzuki coupling of boronic acid 1 with 3-bromo-3-butene-1-ol in the presence of tetrakis triphenylphosphine palladium (0) and a base, such as sodium carbonate, in toluene at 100° C. to provide compound 2. Cyclopropanation of homoallylic alcohol 2 with reagents such as diethyl zinc and chloroiodomethane in dichloroethane provides the cyclopropane compound 3. Oxidation of alcohol 3 with a reagent such as PCC in dichloromethane, provides aldehyde 4. This aldehyde 4 can be treated with a phosphonate, such as the lithium salt of diethyl 3-ethoxycarbonyl-2-methylprop-2-enylphosphonate (mixture of double bond isomers) in THF at reduced temperatures in a Horner-Wadsworth-Emmons olefination reaction to provide the dienoate esters 5. The olefination reaction is preferably conducted in the presence of 1,3-dimethyl-3,4,5,6-tetrahydro-2(1H)-pyrimidinone (DMPU). The acids and salts 6 are readily obtainable from the corresponding esters by hydrolysis in an alkanol solvent at ambient temperature with about a three molar excess of base, for example, potassium hydroxide. Alternatively, the ethyl esters may be hydrolyzed in THF/water or acetone/water at ambient temperature with, for example, excess lithium hydroxide. The hydrolysis solution is acidified and the hydrolysate recovered by conventional means to give as the major product the (2E, 4E)-bicyclic diene carboxylic acid derivatives of structure 6. The minor (2E, 4Z)-bicyclic diene and (2Z, 4E)-bicyclic diene geometric isomers, by-products of the olefination reaction, are readily isolated by silica gel chromatography or HPLC purification of the hydrolysate mixture.

The polysubstituted benzene derivatives of the present invention, that is compounds of general structures 12, may be prepared in accordance with Scheme II. Suzuki coupling of 5 3,5-di-t-butylphenyl-1-triflate 7 for example with 1-[2-t-butyl-dimethylsilanyloxy)-ethyl]-vinyl boronic acid the presence of tetrakis triphenylphosphine palladium (0) and a base, such as sodium carbonate, in toluene at 100° C. provided, after desilylation with for example, TBAF in THF, compound 8. Compound 8 was then elaborated by the same processes as employed in the preparation process of Scheme I, to afford dienoic acid 12.

Scheme III: Synthesis of Compounds of Structure (III):

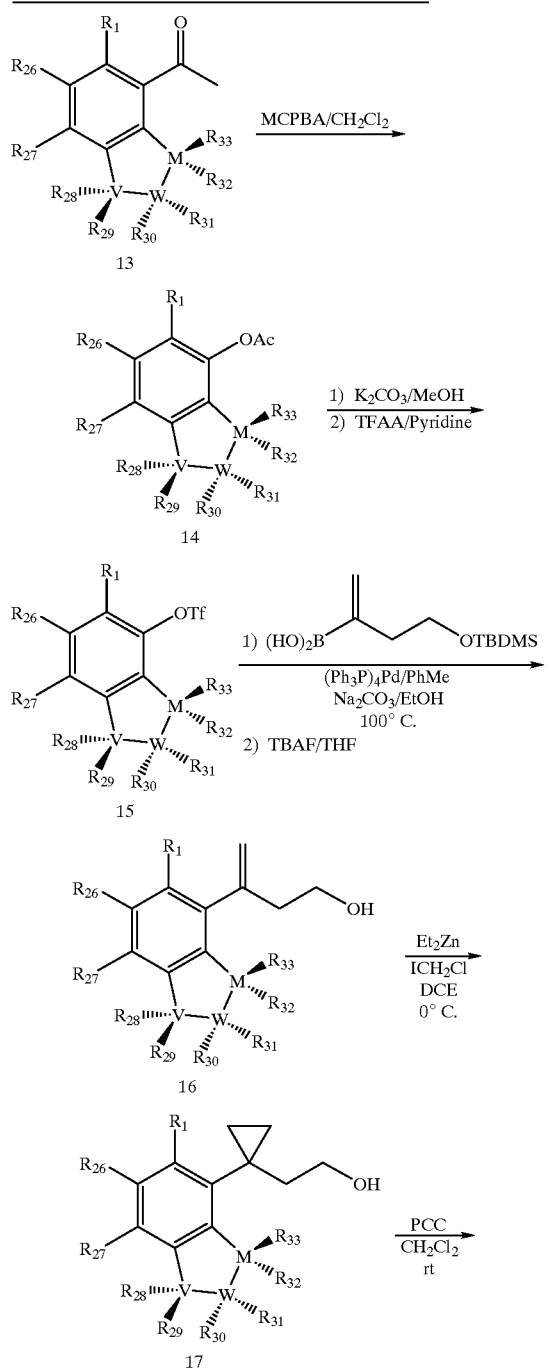

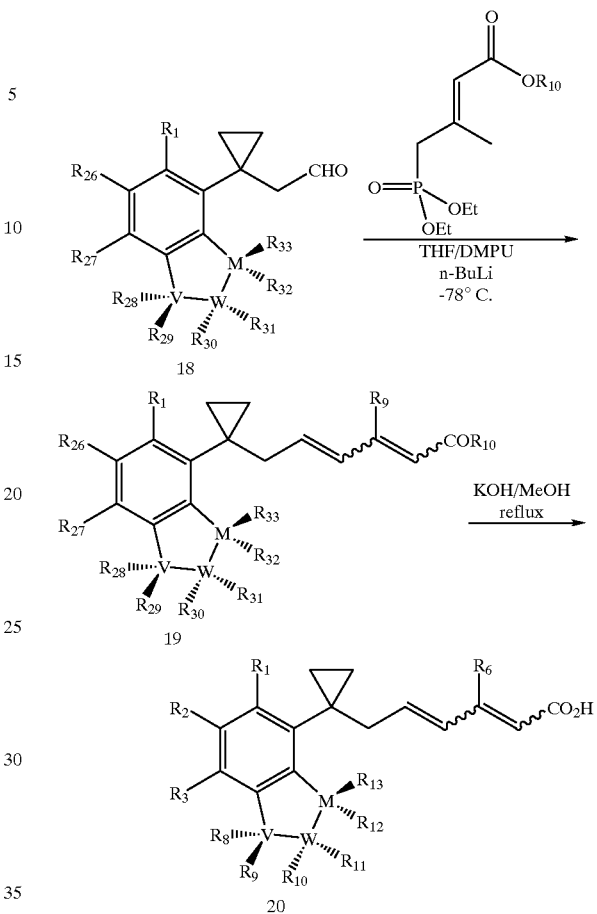

Dienoic acid derivatives such as compound 20 can be obtained in accordance with the reaction Scheme III. Bayer-Villager oxidation of ketone 13 with an oxidant such as MCPBA in dichloromethane gave compound 14. Hydrolysis in an alkanol solvent at ambient temperature with a base such as sodium carbonate, followed by a treatment with for example, triflic anhydride in pyridine provided triflate 15. Compound 15 was then elaborated by the same processes as employed in the preparation process of Scheme II, to afford dienoic acid 20.

Scheme IV: Synthesis of Compounds of Structure (I):

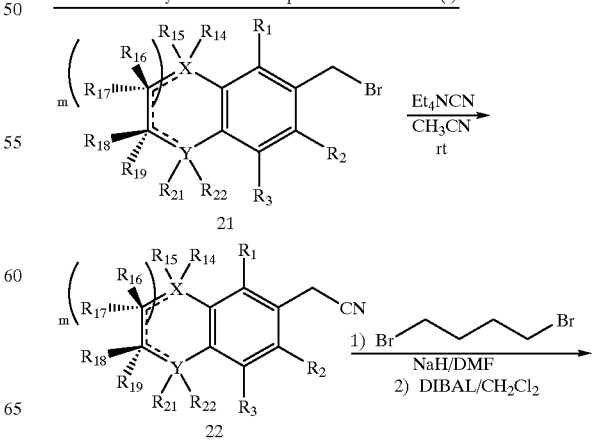

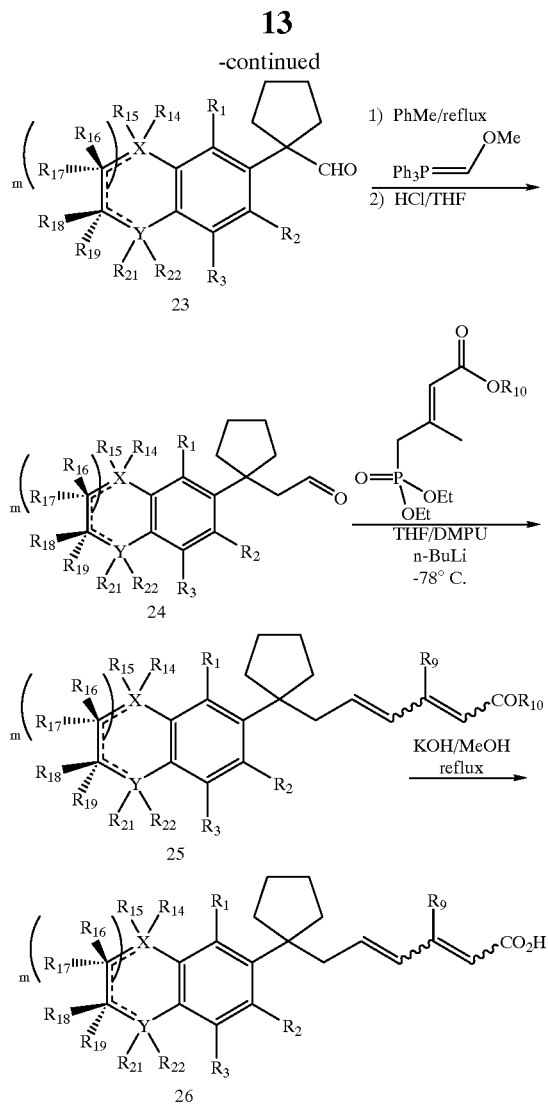

The dienoic acids of the present invention, that is compounds of general structure 26, may be prepared in accordance with reaction Scheme IV. Cyanation of benzyl bromide of general structure 21 with, for example, tetraethyl ammonium cyanide in acetonitrile afforded compound 22. Cyclopentannulation with 1,4-dibromobutane with a base, such as sodium hydride, in DMF followed by reduction with a reducing agent like diisobutyl aluminum hydride gave compound 23. One carbon homologation with (methoxymethyl) triphenylphosphonium bromide-mixture with sodium amide in toluene at reflux in a Wittig olefination reaction provided after hydrolysis, for example with HCl 10% in THF, aldehyde 24. This aldehyde 24 can be treated with a phosphonate, such as the lithium salt of diethyl 3-ethoxycarbonyl-2-methylprop-2-enylphosphonate (mixture of double bond isomers) in THF at reduced temperatures in a Horner-Wadsworth-Emmons olefination reaction to provide the dienoate esters 25. The olefination reaction is preferably conducted in the presence of 1,3-dimethyl-3,4,5,6-tetrahydro-2(1H)-pyrimidinone (DMPU). The acids and salts 26 are readily obtainable from the corresponding esters by hydrolysis in an alkanol solvent at ambient temperature with about a three molar excess of base, for example, potassium hydroxide. Alternatively, the ethyl esters may be hydrolyzed in THF/water or acetone/water at ambient temperature with, for example, excess lithium hydroxide. The hydrolysis solution is acidified and the hydrolysate recovered by conventional means to give as the major product the (2E, 4E)-bicyclic diene carboxylic acid derivatives of structure 26. The minor (2E, 4Z)-bicyclic diene and (2Z, 4E)-bicyclic diene geometric isomers, by-products of the olefination reaction, are readily isolated by silica gel chromatography or HPLC purification of the hydrolysate mixture.

It will be understood by those skilled in the art that certain modifications can be made to the above-described methods that remain within the scope of the present invention. For example, the compounds of the present invention may also be produced in the form of the corresponding amides or esters, or pharmaceutically acceptable salts.

In another aspect, the retinoid compounds of the present invention are combined in a mixture with a pharmaceutically acceptable carrier to provide pharmaceutical compositions useful for treating the biological conditions or disorders noted herein in mammalian, and more preferably, in human patients. The particular carrier employed in these pharmaceutical compositions may take a wide variety of forms depending upon the type of administration desired, e.g., intravenous, oral, topical, suppository or parenteral.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent the most advantageous oral dosage form for the pharmaceutical compositions of the present invention.

For parenteral administration, the carrier will typically comprise sterile water, although other ingredients that aid in solubility or serve as preservatives, may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin, and water in oil emulsions such as Eucerin™ (Beiersdorf). Examples of suitable cream bases are Nivea™ Cream (Beiersdorf), cold cream (USP), Purpose Cream™ (Johnson & Johnson) hydrophilic ointment (USP), and Lubrider™ (Warner-Lambert).

The pharmaceutical compositions and compounds of the present invention will generally be administered in the form of a dosage unit (e.g., tablet, capsule etc.) at from about 1 μg/kg of body weight to about 500 mg/kg of body weight, more preferably from about 10 μg/kg to about 250 mg/kg, and most preferably from about 20 μg/kg to about 100 mg/kg. As recognized by those skilled in the art, the particular quantity of pharmaceutical composition according to the present invention administered to a patient will depend upon a number of factors, including, without limitation, the biological activity desired, the condition of the patient, and tolerance for the drug.

The compounds of this invention also have utility when labeled and used in assays to determine the presence of RARs and RXRs. They are particularly useful due to their ability to selectively bind to members of the RAR and RXR subfamilies and can therefore be used to determine the presence of RAR and RXR isoforms in the presence of other retinoid receptors or related intracellular receptors.

Due to the selective specificity of the compounds of this invention for retinoid receptors, these compounds can also be used to purify samples of RARs and RXRs in vitro. Such purification can be carried out by mixing samples containing retinoid receptors with one or more of the compounds of the present invention, so that the compound (ligand) binds to the receptor, and then separating out the bound ligand/receptor combination by separation techniques which are known to those of skill in the art. These techniques include column separation, filtration, centrifugation, tagging and physical separation, and antibody complexing, among others.

The compounds of the present invention also include racemate, individual stereoisomers and mixtures thereof. These isomers are then isolated by standard resolution techniques, including fractional crystallization and reverse phase and chiral column chromatography.

The compounds and pharmaceutical compositions of the present invention can advantageously be used in the treatment of the diseases and conditions described herein. In this regard, the compounds and compositions will prove particularly useful in the treatment of skin-related diseases and conditions, such as acne, psoriasis, and photo damage, cancerous and precancerous conditions, diseases of the eye, cardiovascular diseases, inflammatory and neurodegenerative diseases, diseases associated with human papilloma virus, improper pituitary function, modulation of apoptosis, diseases of the immune system, wound healing and restoration of hair growth.

Furthermore, the compounds and pharmaceutical compositions of the present invention possess a number of advantages over previously identified retinoid compounds. For example, the compounds are extremely potent activators of RARs and RXRs, preferably displaying 50% maximal activation of one or more of the retinoid receptors at a concentration of less than 100 nM, more preferably at a concentration of less than 50 nM, more preferably yet at a concentration of less than 20 nM, and most preferably at a concentration of less than 10 nM. Also, the RAR and RXR selective compounds of the present invention preferentially activate one subfamily of retinoid receptors at a level at least 2 times greater, preferably at least 5 times greater, more preferably at least 10 times greater, and most preferably at least 100 times greater than the other subfamily of retinoid receptors. In addition, the compounds of the present invention also are easier to synthesize, provide greater stability and bioavailability, and appear to be less teratogenic in comparison to all-trans retinoic acid and 9-cis retinoic acid, known RAR and RXR active compounds, respectively.

The invention will be further illustrated by reference to the following non-limiting Examples.

EXAMPLE 1

(2E, 4E)-6-[1-(5,5,8,8-Tetramethyl-5,6,7,8-tetrahydronaphtha-len-2-yl) cyclopropanyl]-3-methyl hexadienoic acid (Compound 101)(Structure I, compound 6: $R_2$=H, prepared as illustrated and described in Scheme 1)

To a solution of 2-bromobenzene (40 g, 255 mmol) and 2,5-dichloro-dimethyl hexane (52.7 g, 280 mmol) in 600 mL anhydrous $CH_2Cl_2$ at 5° C. was added, portionwise, $AlCl_3$ (10.2 g, 76 mmol). Upon addition of $AlCl_3$, HCl gas evolution was observed. The solution changed from yellow to reddish orange. The reaction solution was kept at 5–20° C. for two hours and then allowed to stir at room temperature overnight. The reaction mixture was poured into 600 g of ice and extracted with $CHCl_3$ (2×700 mL). The organic phase was washed with water, aqueous saturated $NaHCO_3$, saturated NaCl and dried ($Na_2SO_4$). The organic solution was then concentrated in vacuo and chromatographed (hexane) to provide 50 g of 2-bromo-5,5,8,8-tetramethyl-5,6,7,8-tetrahydronaphthalene as a yellow gummy solid in 73% yield. $^1$H NMR (400 MHz, $CDCl_3$) δ7.41 (d, J=2.0 Hz, 1H, aromatic), 7.22 (dd, J=8.0 and 1.9 Hz, 1H, aromatic), 7.18 (d, J=8.0 Hz, 1H, aromatic), 1.68 (s, 4H, 2$CH_2$), 1.27 (s, 6H, 2$CH_3$), 1.24 (s, 6H, 2$CH_3$).

To a solution of the above aryl bromide (50 g, 187 mmol) in 600 mL of anhydrous THF at −78° C., was added n-BuLi (175.4 mL, 281 mmol), generating a pale yellow solution. This reaction solution was stirred at −78° C. for 45 minutes. Trimethyl borate (42.5 mL, 374 mmol) was then added via a syringe. The reaction mixture was allowed to warm to room temperature and stirred overnight. It was then cooled to 0° C. and acidified with 5% HCl1 to pH=6. The organic phase was concentrated in vacuo and the residue was diluted with 600 mL of water and extracted with $CH_2Cl_2$ (3×500 mL). The organic phase was washed with brine and dried ($MgSO_4$). After removal of the solvent, 30 g of the boronic acid (1: $R_2$=H) was isolated as a white gum in 69% yield. To a solution of tetrakistriphenylphosphine palladium (0.098 g, 0.072 mmol) in 6 mL of toluene under $N_2$ was added 3-bromo-3-buten-1-ol (0.24 mL, 2.4 mmol) at room temperature. The mixture was allowed to stir for 10 min. The above boronic acid (1.0 g, 4.3 mmol) in 3 mL of ethanol was added, followed by 3.6 mL of an aqueous 2M solution of $Na_2CO_3$. The reaction mixture was then refluxed for four hours after which the solvent was removed in vacuo to give an oil. The residue was then dissolved in 75 mL of EtOAc and washed with water and saturated NaCl aqueous solution, dried ($Na_2SO_4$) and concentrated it vacuo to an oil that was subjected to chromatography (20% EtOAc/80% hexane) to give 506 mg (43%) of 3-(5,5,8,8-tetramethyl-3-propyloxy-5,6,7,8-tetrahydronaphthalen-2-yl)-3-buten-1-ol (2: $R_2$=H). $^1$H NMR (400 MHz, $CDCl_3$) δ7.35 (d, J=1.9 Hz, 1H, aromatic), 7.26 (d, J=8.1 Hz, 1H, aromatic), 7.19 (dd, J=8.4 and 2.2 Hz, 1H), 5.40 (s, 1H, olefinic) 5.10 (s, 1H, olefinic), 3.75 (q, J=6.2 Hz, 2H, $CH_2OH$), 2.78 (t, J=5.8 Hz, 2H, allylic-$CH_2$), 1.68 (s, 4H, 2$CH_2$), 1.43 (t, J=5.8 Hz 1H, OH), 1.29 (s, 6H, 2×$CH_3$), 1.28 (s, 6H, 2$CH_2$).

In a 15 mL round-bottom flask (oven dried and under argon) was added anhydrous dichloroethane (6 mL) and diethyl zinc (0.34 mL, 3.3 mmol). The mixture was cooled to 0° C. and chloroiodomethane (0.43 mL, 6.0 mmol) was slowly added via syringe. The reaction mixture was stirred at 0° C. for 5 min. and a solution of the above homoallylic alcohol (2: $R_2$=H; 0.41 g, 1.57 mmol) in dichloroethane (2 mL) was slowly added. The mixture was allowed to warm to room temperature and stirred for one hour. The reaction mixture was then quenched with saturated $NH_4Cl$ and the aqueous phase was extracted with EtOAc (2×15 mL). The organic solution was washed with saturated NaCl, dried ($Na_2SO_4$) and concentrated in vacuo. Crude [1-(5,5,8,8-tetramethyl-3-propyloxy-5,6,7,8-tetrahydronaphthalen-2-yl)-cyclopropyl]ethanol (3: $R_2$=H) was recovered in 63% yield (0.27 g) and carried directly on to the next step. To a solution of the above cyclopropyl alcohol (3: $R_2$=H; 0.25 g, 0.92 mmol) in 5 mL $CH_2Cl_2$ at room temperature was added PCC (0.4 g, 1.84 mmol). The reaction mixture was stirred for 3 hours and then filtered and rinsed with 15% EtOAc/hexane through a pad of celite/silica gel. Solvent was removed in vacuo to provide 230 mg of 1-(5,5,8,8-tetramethyl-5,6,7,8-tetrahydronaphthalen-2-yl)-cyclopropaneacetaldehyde (4: $R_2$=H) as a white solid in 93% yield. $^1$H NMR (400 MHz, $CDCl_3$) δ9.78 (t, J=2.5 Hz, 1H, aldehyde), 7.20 (d, J=8.1 Hz, 1H, aromatic), 7.18 (d, J=2.0 Hz, 1H, aromatic), 6.99 (dd, J=8.1 and 2.1 Hz, 1H, aromatic), 2.57 (d, J=2.6 Hz, 2H, $CH_2$), 1.66 (s, 4H, $2CH_2$), 1.26 (s, 6H, $2CH_3$), 1.25 (s, 6H, $2CH_3$), 1.02 (dd, J=6.4, 4.7 Hz, 2H, $CH_2$), 0.87 (dd, J=6.1,4.6 Hz, 2H, $CH_2$).

A solution 3-ethoxycarbonyl-2-methylprop-2-enylphosphonate (674 mg, 2.55 mmol) in THF/DMPU (1:1; 7 mL) at −78° C. was treated with n-BuLi (2.5 M in hexane; 1.02 mL, 2.55 mmol). The reaction mixture was stirred for ten minutes. The above cyclopropanecarboxaldehyde (230 mg, 0.851 mmol) in THF/DMPU (5 mL of 1:1 mixture) was added. The reaction mixture was warmed to 0° C. and monitored by TLC. The reaction was complete in 30 minutes and was quenched with saturated aqueous $NH_4Cl$. The aqueous layer was extracted with EtOAc (2×20 mL). The combined organic solution was washed with saturated NaCl and dried ($Na_2SO_4$). The recovered oil was then filtered through a short plug of silica gel and further rinsed with 5% ethyl acetate/hexane to remove DMPU. A mixture of isomers (231 mg) of ethyl-6-[(5,5,8,8-tetramethyl-5,6,7,8-tetrahydronaphthalen-2-yl)cyclopropan-1-yl]-3-methyl-2,4-hexadienoate (5: $R_2$=H) was recovered in 75% yield.

To a solution of the above ester (231 mg, 0.63 mmol) in 10 mL of MeOH was added 40 drops of 6.4M KOH (excess). The reaction mixture was allowed to reflux for three hours. The MeOH was then evaporated in vacuo and the residue was diluted in 6 mL of water. The aqueous phase was neutralized with 5% HCl to pH=6. The aqueous phase was then extracted with EtOAc (2×15 mL). The organic phase was dried ($Na_2SO_4$) and concentrated in vacuo. The final product was recrystallized from $Et_2O$/hexane (1:2) to give 97 mg (46%) of (2E, 4E)-6-[2-(5,5,8,8-tetramethyl-5,6,7,8-tetrahydrona-phthalen-2-yl)-cyclopropyl]-3-methyl-2,4-hexadienoic acid (6: $R_2$=H). $^1$H NMR (400 MHz, $CDCl_3$) δ7.19 (d, J=8.1 Hz, 1H, aromatic), 7.15 (d, J=1.9 Hz, 1H, aromatic), 6.98 (dd, J=8.1 and 1.9 Hz, 1H, aromatic), 6.15 (dt, J=15.7 and 6.8 Hz, 1H, olefinic CH), 6.07 (d, J=15.7 Hz, 1H, olefinic CH), 5.67 (s, 1H, olefinic CH), 2.41 (d, J=6.8 Hz, 2H, $CH_2$), 2.23 (s, 3H, $CH_3$), 1.66 (s, 4H, $2CH_2$), 1.26 (s, 6H, $2CH_3$), 1.24 (s, 6H, $2CH_3$), 0.84 (dd, J=6.3,4.7 Hz, 2H, $CH_2$), 0.73 (dd, J=5.6, 4.0 Hz, 2H, $CH_2$).

EXAMPLE 2

(2E, 4E)-6-[(3,5,5,8,8-Pentamethyl-5,6,7,8-tetrahydronaphthalen-2-yl) cyclopropan-1-yl]-3-methyl hexadienoic acid (Compound 102)(Structure I, compound 6: $R_2$=Me, prepared as illustrated and described in Scheme 1)

The 2-bromo-3,5,5,8,8-tetramethyl-5,6,7,8-tetrahydro naphthalene (1.0 g, 3.56 mmol) was converted to the corresponding boronic acid (1: $R_2$=Me) as described for Example 1 to give 860 mg of a white solid in 98% yield. The crude mixture was carried on to the next step.

The above boronic acid (1: $R_2$=Me; 0.5 g, 2.0 mmol) was coupled with 3-bromo-3-butenol as described in Example 1 to give 182 mg of 3-(3,5,5,8,8-pentamethyl-5,6,7,8-tetrahydronaphthalen-2-yl)-3-buten-1-ol (2: $R_2$=Me) as a white solid in 33% yield after column chromatography (10 to 15% EtOAc/hexane). $^1$H NMR (400 MHz, $CDCl_3$) δ7.07 (s, 1H, aromatic), 6.98 (s, 1H, aromatic), 5.23 (s, 1H, olefinic CH), 4.99 (s, 1H, olefinic CH), 3.64 (t, J=6.4 Hz, 2H, $CH_2$), 2.59 (t, J=6.2 Hz, 2H, $CH_2$), 2.23 (s, 3H, $CH_3$), 1.66 (s, 4H, $2CH_2$), 1.27 (s, 6H, $2CH_3$), 1.25 (s, 6H, $2CH_3$.

The above unsaturated alcohol (2: $R_2$=Me; 0.15 g, 0.60 mmol) was converted to the cyclopropyl alcohol as described in Example 1 to give 73 mg of [1-(3,5,5,8,8-pentamethyl-5,6,7,8-tetrahydronaphthalen-2-yl)-cyclopropyl]-ethanol (3: $R_2$=Me) as a pale yellow oil in 42% yield. $^1$H NMR (400 MHz, $CDCl_3$) δ7.10 (s, 1H, aromatic), 7.02 (s, 1H, aromatic), 3.61 (broad t, 2H, $CH_2$), 2.37 (s, 3H, $CH_3$), 1.72 (bs, 2H, $CH_2$), 1.61 (s, 4H, $2CH_2$), 1.24 (s, 12H, $4CH_3$), 1.19 (bs, 1H, OH), 0.75 (m, 4H, $2CH_2$). The above cyclopropyl alcohol (0.072 g, 0.252 mmol) was oxidized as described in Example 1 to give 70 mg of 1-(3,5,5,8,8-pentamethyl-5,6,7,8-tetrahydronaphthalen-2-yl)-cyclopropaneacetaldehyde (4: $R_2$=Me) as a white solid in 95% yield The above cyclopropyl aldehyde (4: $R_2$=Me; 0.07 g, 0.246 mmol) and 3-ethoxycarbonyl-2-methylprop-2-enylphosphonate (195 mg, 0.739 mmol) were condensed as described for Example 1 to give 92 mg of ethyl-6-[2-(3,5, 5,8,8-pentamethyl-5,6,7,8-tetrahydronaphthalen-2-yl)-cyclopropyl]-3-methyl-2,4-hexadienoate (5: $R_2$=Me) as a pale yellow oil in 98% yield.

The above ethyl ester (5: $R_2$=Me; 0.092 g, 0.24 mmol) in 3 mL MeOH was hydrolyzed as described for Example 1 to give the crude acid. The crude mixture was recrystallized from $Et_2O$/Hex (1:2) to give 22 mg (26%) of (2E, 4E)-6-[2-(3,5,5,8,8-pentamethyl-5,6,7,8-tetrahydronaphthalen-2-yl)-cyclopropyl]-3-methyl-2,4-hexadienoic acid (6: $R_2$=Me). $^1$H NMR (400 MHz, $CDCl_3$) δ7.06 (s, 1H, aromatic), 7.02 (s, 1H, aromatic), 6.08 (dt, J=15.6 and 7.0 Hz, 1H, olefinic CH), 5.96 (d, J=15.6 Hz, 1H, olefinic CH), 5.66 (s, 1H, olefinic CH), 2.38 (s, 3H, $CH_3$), 2.30 (d, J=7.1 Hz, 2H, $CH_2$), 2.22 (s, 3H, $CH_3$), 1.64 (s, 4H, 2CH2), 1.25 (s, 6H, $2CH_3$), 1.22 (s, 6H, $2CH_3$), 0.75 (m, 4H, $2CH_2$).

EXAMPLE 3

(2E, 4E)-6-[(5,5,8,8-Tetramethyl-3-methoxy-5,6,7,8-tetrahydronaphtha-len-2-yl) cyclopropan-1-yl]-3-methyl hexadienoic acid (Compound 103)(Structure I, compound 6: $R_2$=OMe, prepared as illustrated and described in Scheme 1)

The 2-bromo-5,5,8,8-tetramethyl-3-methoxy-5,6,7,8-tetrahydro naphthalene (2.97 g, 9.8 mmol) was converted to the corresponding boronic acid (1: $R_2$=OMe) as described for Example 1 to give 2.26 g of a white solid in 88% yield. The crude mixture was carried on to the next step.

The above boronic acid (1: $R_2$=OMe; 1.12 g, 4.26 mmol) was coupled with 3-bromo-3-butenol as described in Example 1 to give 456 mg of 3-(5,5,8,8-tetramethyl-3-methoxy-5,6,7,8-tetrahydronaphthalen-2-yl)-3-buten-1-ol (2: $R_2$=OMe) as a white solid in 34% yield after column chromatography (10 to 15% EtOAc/hexane). $^1$H NMR (400 MHz, $CDCl_3$) δ7.02 (s, 1H, aromatic), 6.79 (s, 1H, aromatic), 5.23 (s, 1H, olefinic CH), 5.13 (s, 1H, olefinic CH), 3.98 (s, 3H, $OCH_3$), 3.61 (q, J=6.1 Hz, 2H, $CH_2$), 2.69 (t, J=6.0 Hz, 2H, $CH_2$), 1.81 (t, J=6.2 Hz, 1H, OH), 1.67 (m, 4H, $2CH_2$), 1.29 (s, 6H, $2CH_3$), 1.25 (s, 6H, $2CH_3$).

The above unsaturated alcohol (2: $R_2$=OMe; 0.156 g, 0.49 mmol) was converted to the cyclopropyl alcohol as described in Example 1 to give 146 mg of [1-(5,5,8,8-tetramethyl-3-methoxy-5,6,7,8-tetrahydronaphthalen-2-yl)-cyclopropyl]-ethanol (3: $R_2$=OMe) as a pale yellow oil in 98% yield. $^1$H NMR (400 MHz, $CDCl_3$) δ7.18 (s, 1H, aromatic), 6.72 (s, 1H, aromatic), 3.85 (s, 3H, $OCH_3$), 3.53 (q, J=6.1 Hz, 2H, $CH_2$), 2.61 (t, J=6.7 Hz, 1H,OH), 1.73 (t, J=5.9 Hz, 2H, $CH_2$), 1.65 (s, 4H, $2CH_2$), 1.27 (s, 6H, $2CH_3$), 1.24 (s, 6H, 2 $CH_3$), 0.74 (m, 4H, $2CH_2$). The above cyclopropyl alcohol (167 mg, 0.55 mmol) was oxidized as described in Example 1 to give 150 mg of 1-(5,5,8,8-tetramethyl-3-methoxy-5,6,7,8-tetrahydro-naphthalen-2-yl)-cyclopropane acetaldehyde (4: $R_2$=OMe) as a white solid in 90% yield.

The above cyclopropyl aldehyde (4: $R_2$=OMe; 0.15 g, 0.50 mmol) and 3-ethoxycarbonyl-2-methylprop-2-enylphosphonate (790 mg, 3 mmol) were condensed as described for Example 1 to give 195 mg of ethyl-6-[2-(5,5,8,8-tetramethyl-3-methoxy-5,6,7,8-tetrahydronaphthalen-2-yl)-cyclopropyl]-3-methyl-2,4-hexadienoate (5: $R_2$=OMe) as a pale yellow oil in 93% yield.

The above ethyl ester (5: $R_2$=OMe; 0.195 g, 0.45 mmol) in 7 mL MeOH was hydrolyzed as described for Example 1 to give the crude acid. The crude mixture was recrystallized from $Et_2O$/Hex (1:2) to give 87 mg (51%) of (2E, 4E)-6-[2-(5,5,8,8-tetramethyl-3-methoxy-5,6,7,8-tetrahydronaphthalen-2-yl)-cyclopropyl]-3-methyl-2,4-hexadienoic acid (6: $R_2$=OMe). $^1$H NMR (400 MHz, $CDlC_3$) δ7.04 (s, 1H, aromatic), 6.70 (s, 1H, aromatic), 6.10 (dt, J=15.4 and 7.1 Hz, 1H, olefinic CH), 5.96 (d, J=15.4 Hz, 1H, olefinic CH), 5.64 (s, 1H, olefinic CH), 3.83 (s, 3H, O $CH_3$), 2.35 (d, J=7.1 Hz, 2H, $CH_2$), 2.20 (s, 3H, $CH_3$), 1.64 (s, 4H, 2CH2), 1.27 (s, 6H, $2CH_3$), 1.21 (s, 6H, $2CH_3$), 0.75 (m, 4H, $2CH_2$).

EXAMPLE 4

(2E, 4E)-6-[(5,5,8,8-Tetramethyl-3-ethoxy-5,6,7,8-tetrahydronaphthalen-2-yl) cyclopropan-1-yl]-3-methyl hexadienoic acid (Compound 104)(Structure I, compound 6: $R_2$=OEt, prepared as illustrated and described in Scheme 1)

The 2-bromo-5,5,8,8-tetramethyl-3-ethoxy-5,6,7,8-tetrahydro naphthalene (2.0 g6.3 mmol) was converted to the corresponding boronic acid (1: $R_2$=OEt) as described for Example 1 to give 1.78 g of a yellow oil in 95% yield. The crude mixture was carried on to the next step.

The above boronic acid (1: $R_2$=OEt; 890 mg, 3.16 mmol) was coupled with 3-bromo-3-butenol as described in Example 1 to give 316 mg of $^3$-(5,5,8,8-tetramethyl-3-ethoxy-5,6,7,8-tetrahydronaphthalen-2-yl)-3-buten-1-ol (2: $R_2$=OEt) as a white solid in 33% yield after column chromatography (10 to 15% EtOAc/hexane). $^1$H NMR (400 MHz, $CDCl_3$) δ7.02 (s, 1H, aromatic), 6.75 (s, 1H, aromatic), 5.22 (s, 1H, olefinic CH), 5.12 (s, 1H, olefinic CH),4.03 (q, J=7.1 Hz, 2H, $CH_2$), 3.62 (q, J=6.1 Hz, 2H, $CH_2$), 2.70 (t, J=6.1 Hz, 2H, $CH_2$), 1.90 (t, J=6.2 Hz, 1H, OH), 1.66 (s, 4H, $2CH_2$), 1.38 (t, J=7.2 Hz, 3H, $CH_3$), 1.28 (s, 6H, $2CH_3$), 1.24 (s, 6H, $2CH_3$.

The above unsaturated alcohol (2: $R_2$=OEt; 316 mg, 1.04 mmol) was converted to the cyclopropyl alcohol as described in Example 1 to give 218 mg of [1-(5,5,8,8-tetramethyl-3-ethoxy-5,6,7,8-tetrahydronaphthalen-2-yl)-cyclopropyl]-ethanol (3: $R_2$=OEt) as a pale yellow oil in 66% yield. $^1$H NMR (400 MHz, $CDCl_3$) δ7.18 (s, 1H, aromatic),6.70 (s, 1H, aromatic), 4.06 (q, J=7.0 Hz, 2H, $C_2$), 3.53 (q, J=6.1 Hz, 2H, $CH_2$), 2.80 (t, J=6.8 Hz, 1H, OH), 1.71 (t, J=6.8 Hz, 2H, $CH_2$), 1.64 (s, 4H, $2CH_2$), 1.45 (t, J=6.8 Hz, 3H, $CH_3$), 1.25 (s, 6H, $2CH_3$), 1.23 (s, 6H, 2 $CH_3$), 0.74 (d, J=3.5 Hz, 4H, $2CH_2$). The above cyclopropyl alcohol (218 mg, 0.69 mmol) was oxidized as described in Example 1 to give 198 mg of 1-(5,5,8,8-tetramethyl-3-ethoxy-5,6,7,8-tetrahydro-naphthalen-2-yl)-cyclopropaneacetaldehyde (4: $R_2$=OEt) as a white solid in 91% yield.

The above cyclopropyl aldehyde (4: $R_2$=OEt; 0.198 g, 0.63 mmol) and 3-ethoxycarbonyl-2-methylprop-2-enylphosphonate (500 mg, 1.89 mmol) were condensed as described for Example 1 to give 229 mg of ethyl-6-[2-(5,5,8,8-tetramethyl-3-ethoxy-5,6,7,8-tetrahydronaphthalen-2-yl)-cyclopropyl]-3-methyl-2,4-hexadienoate (5: $R_2$=OEt) as a pale yellow oil in 89% yield.

The above ethyl ester (5: $R_2$=OEt; 0.229 g, 0.56 mmol) in 10 mL MeOH was hydrolyzed as described for Example 1 to give the crude acid. The crude mixture was recrystallized from $Et_2O$/Hex (1:2) to give 100 mg (60%) of (2E, 4E)-6-[2-(5,5,8,8-tetramethyl-3-ethoxy-5,6,7,8-tetrahydronaphthalen-2-yl)-cyclopropyl]-3-methyl-2,4-hexadienoic acid (6: $R_2$=OEt). $^1$H NMR (400 MHz, $CDCl_3$) δ7.03 (s, 1H, aromatic), 6.69 (s, 1H, aromatic), 6.10 (dt, J=15.5 and 7.2 Hz, 1H, olefinic CH), 5.96 (d, J=15.5 Hz, 1H, olefinic CH), 5.64 (s, 1H, olefinic CH), 4.04 (q, J=7.1 Hz, 2H, $CH_2$), 2.37 (d, J=7.2 Hz, 2H, $CH_2$), 2.20 (s, 3H, $CH_3$), 1.64 (s, 4H, 2CH2), 1.42 (t, J=7.2 Hz, 3H, $CH_3$), 1.26 (s, 6H, $2CH_3$), 1.22 (s, 6H, $2CH_3$), 0.73 (m, 2H, $CH_2$), 0.66 (m, 2H, $CH_2$).

EXAMPLE 5

(2E, 4E)-6-[(3,5-di-t-butyl phenyl) cyclopropan-1-yl]-3-methyl hexadienoic acid (Compound 105)
(Structure II, compound 12: $R_3$=$R_8$=t-Bu, prepared as illustrated and described in Scheme 2)

The 3,5-di-t-butylphenyl-1-triflate (7; R=OTf) (200 mg, 0.71 mmol) was coupled with 3-(t-butyldimethylsilyloxybutene) boronic acid (M=$B(OH)_2$) as described in Example 1 to give, after desilylation with tetrabutylammonium fluoride in THF, 70 mg of 3-(3,5-di-t-butyl phenyl)-3-buten-1-ol (8) as a pale yellow oil in 42% yield after column chromatography (10 to 15% EtOAc/hexane). $^1$H NMR (400 MHz, $CDCl_3$) δ7.38 (d, J=1.7 Hz, 1H, aromatic), 7.25 (d, J=1.8 Hz, 1H, aromatic), 5.41 (d, J=1.4 Hz, 1H, vinylic CH), 5.15 (d, J=1.3 Hz, 1H, vinylic CH), 3.77 (q, J=12.4, 6.2 Hz, 2H, aliphatic $CH_2$), 2.82 (t, J=6.4 Hz, 2H, allylic $CH_2$), 1.57 (t, J=6.2 Hz, 1H, alcohol), 1.44 (s, 18H aliphatic $6CH_2$).

The above unsaturated alcohol 8 (70 mg, 0.34 mmol) was converted to the cyclopropyl alcohol as described in Example 1 to give 29 mg of [1-(3,5-di-t-butyl phenyl)-cyclopropyl]-ethanol (9) as a pale yellow oil in 40% yield. $^1$H NMR (400 MHz, $CDCl_3$) δ7.25 (d, J=1.8 Hz, 1H, aromatic), 7.15 (d, J=1.8 Hz, 2H, aromatic), 3.65 (q, J=12.5, 6.7 Hz, 2H, aliphatic $CH_2$), 1.83 (t, J=6.9 Hz, 2H, aliphatic $CH_2$), 1.31 (s, 18H, aliphatic $6CH_2$), 1.18 (t, J=5.6 Hz, 1H, alcohol), 0.84 (dd, J=9.9, 4.5 Hz, 2H, aliphatic $CH_2$), 0.71 (dd, J=10.0, 3.9 Hz, 2H, aliphatic $CH_2$). The above cyclopropyl alcohol (29 mg, 0.13 mmol) was oxidized as described in Example 1 to give 29 mg of 1-(3,5-di-t-butyl phenyl)-cyclopropaneacetaldehyde (10) as a clear oil in 100% yield. $^1$H NMR (400 MHz, $CDCl_3$) δ9.79 (t, J=2.6 Hz, 1H, aldehyde), 7.25 (s, 1H, aromatic), 7.12 (d, J=1.3 Hz, 2H, aromatic), 2.59 (d, J=2.5 Hz, 2H, aliphatic CH2), 1.31 (s, 18H, aliphatic $6CH_2$), 1.04 (dd, J=10.7, 5.2 Hz, 2H, aliphatic $CH_2$), 0.88 (dd, J=10.6, 5.5 Hz, 2H, aliphatic $CH_2$).

The above cyclopropyl aldehyde 10 (29 mg, 0.13 mmol) and 3-ethoxycarbonyl-2-methylprop-2-enylphosphonate (215 mg, 0.82 mmol) were condensed as described for Example 1 to give 33 mg of ethyl-6-[1-(3,5-di-t-butyl phenyl)-cyclopropyl]-3-methyl-2,4-hexadienoate (11) as a pale yellow oil in 97% yield.

The above ethyl ester 11 (33 mg, 0.09 mmol) in 1.5 mL MeOH was hydrolyzed as described for Example 1 to give the crude acid. The crude mixture was purified by HPLC (82% MeOH/18% 10 mmol NH$_4$OAc+0.3% AcOH) to give 14 mg (45%) of pure (2E, 4E)-6-[1-(3,5-di-t-butyl phenyl)-cyclopropyl]-3-methyl-2,4-hexadienoic acid (12). 1H NMR (400 MHz, CDCl$_3$) δ7.24 (d, J=2.8 Hz, 1H, aromatic), 7.10 (d, J=1.8 Hz, 2H, aromatic), 6.17 (dt, J=15.6 and 7.0 Hz, 1H, vinylic CH), 6.03 (d, J=15.6 Hz, 1H, vinylic CH), 5.68 (s, 1H, vinylic CH), 2.41 (d, J=7.0 Hz, 2H, allylic CH$_2$), 2.24 (s, 3H, aliphatic CH$_3$), 1.31 (s, 18H, aliphatic 6CH$_3$), 0.88 (dd, J=11.2, 7.1 Hz, 2H, aliphatic CH$_2$), 0.74 (dd, J=10.2, 4.1 Hz, 2H, aliphatic CH$_2$).

EXAMPLE 6

(2E, 4E)-6-[(3,4-diethyl phenyl) cyclopropan-1-yl]-3-methyl hexadienoic acid (Compound 106)
(Structure II, compound 12: R$_8$=R$_9$=Et, prepared as illustrated and described in Scheme 2)

In a 50 mL three necked flask fitted with a ground glass joint was placed 1,2-dimethylbenzene (5.0 g, 37.3 mmol), clean iron filings (0.44 g, 7.8 mmol), and a crystal of iodine. The flask was fitted with a dropping funnel, a condenser and a thermometer. The top of the condenser is connected to a gas-absorption trap containing 10% Na$_2$CO$_3$. Mixture is stirred and cooled in an ice-salt mixture. Bromine is added dropwise over a 30 min. period. (During this time, internal temp. Is maintained at 0° C. To −5° C.) Temperature higher than 10° C. Will increase amount of di bromo compound formed. After all the bromine has been added, the reaction mixture is allowed to stand overnight. Poured reaction mixture into water (50 mL), diluted with hexanes (2×50 mL), washed with water (50 mL), washed with 3% NaOH (2×50 mL), washed with water (50 mL), and dried organics with Na$_2$SO$_4$. Organics were concentrated in vacuo to recover the desired product in 76% yield. $^1$H NMR showed that product was pure enough to carry on to the next step without further purification. $^1$H NMR (400 MHz, CDCl$_3$) δ7.28 (d, J=2.1 Hz, 1H, aromatic), 7.24 (dd, J=8.2, 2.1 Hz, 1H, aromatic), 7.01 (d, J=8.1 Hz, 1H, aromatic), 2.60 (m, 4H, aliphatic 2CH$_2$), 1.20 (m, 6H, aliphatic 2CH$_3$).

To a solution of the diethyl bromobenzene (3.0 g, 14.08 mmol) in 60 mL of anhydrous THF at −78° C., was added n-BuLi (9.70 mL, 15.49 mmol), generating a pale yellow solution. This reaction solution was stirred at −78° C. For 15–20 minutes. Trimethyl borate (1.60 rnd., 14.08 mmol) was then added via a syringe. The reaction mixture was allowed to warm to room temperature and stirred overnight. It was then cooled to 0° C. And acidified with 5% HCl to pH=6. The organic phase was concentrated in vacuo and the residue was diluted with 50 mL of water and extracted with CH$_2$Cl$_2$ (3×25 mL). The organic phase was washed with brine and dried with MgSO4. After removal of the solvent, 1.22 g of the boronic acid (7; R=B(OH)$_2$) was isolated as an off-white solid in 72% yield. The crude boronic acid was carried on to the next step without further purification.

The 1-(3,4-diethyl benzene) boronic acid (7; R=B(OH)$_2$) (1.81 g, 10.2 mmol) was coupled with 3-bromo-3-buten-1-ol (M=Bra) as described in Example 1 to give 930 mg of 3-(3,4-diethyl benzene)-3-buten-1-ol (8) as a pale yellow oil in 45% yield after column chromatography (10 to 15% EtOAc/hexane). $^1$H NMR (400 MHz, CDCl$_3$) δ7.22 (d, J=2.7 Hz, 1H, aromatic), 7.20 (dd, J=6.0, 3.9 Hz, 1H, aromatic), 7.13 (d, J=7.8 Hz, 1H, aromatic), 5.40 (d, J=1.5 Hz, 1H, vinylic CH), 5.11 (d, J=1.1 Hz, 1H, vinylic CH), 3.74 (q, J=12.5, 6.3 Hz, 2H, aliphatic CH$_2$), 2.79 (t, J=6.0 Hz, 2H, allylic CH$_2$), 2.65 (m, 4H. Aliphatic 2CH$_2$), 1.41 (t, J=6.0 Hz, 1H, alcohol), 1.22 (m, 6H, aliphatic 2CH$_3$).

The above unsaturated alcohol 8 (930 mg, 4.55 mmol) was converted to the cyclopropyl alcohol as described in Example 1 to give 900 mg of [1-(3,4-diethyl benzene)-cyclopropyl]-ethanol (9) as a pale yellow oil in 91% yield. The above cyclopropyl alcohol (900 mg, 4.12 mmol) was oxidized as described in Example 1 to give 520 mg of 1-(3,4-diethyl benzene) cyclopropaneacetaldehyde (10) as a clear oil in 58% yield. $^1$H NMR (400 MHz, CDCl$_3$) δ9.77 (t, J=2.5 Hz, 1H, aldehyde), 7.08 (m, 3H, aromatic), 2.62 (m, 4H, aliphatic 2CH$_2$), 2.59 (d, J=2.8 Hz, 2H, aliphatic CH$_2$), 1.20 (m, 6H, aliphatic, 2CH$_3$), 1.02 (dd, J=6.3, 4.9 Hz, 2H, aliphatic CH$_2$), 0.87 (dd, J=6.0, 4.4 Hz, 2H, aliphatic CH$_2$).

The above cyclopropyl aldehyde 10 (520 mg, 2.4 mmol) and 3-ethoxycarbonyl-2-methylprop-2-enylphosphonate (2.53 g, 9.6 mmol) were condensed as described for Example 1 to give 712 mg of ethyl-6-[1-(3,4-diethylbenzene)-cyclopropyl]-3-methyl-2,4-hexadienoate (11) as a pale yellow oil in 91% yield.

The above ethyl ester 11 (712 mg, 2.18 mmol) in 35 mL MeOH was hydrolyzed as described for Example 1 to give the crude acid. The crude mixture was purified by HPLC (80% MeOH/20% 10 mmol NH$_4$OAc+0.3% AcOH) to give 390 mg (60%) of pure (2E, 4E)-6-[1-(3,4-diethylbenzene)-cyclopropyl]-3-methyl-2,4-hexadienoic acid (12). $^1$H NMR (400 MHz, CDCl$_3$) δ7.04 (m, 3H, aromatic), 6.15 (dt, J=15.6 and 6.8 Hz, 1H, vinylic CH), 6.05 (d, J=15.6 Hz, 1H, vinylic CH), 5.69 (s, 1H, vinylic CH), 2.62 (q, J=7.5 Hz, 4H, aliphatic 2CH$_2$), 2.43 (d, J=6.8 Hz, 2H, allylic CH$_2$), 2.23 (s, 3H, aliphatic CH$_3$), 1.20 (m, 6H, aliphatic 2CH$_3$), 0.84 (dd, J=6.2, 4.7 Hz, 2H, aliphatic CH$_2$), 0.73 (dd, J=5.4, 4.1 Hz, 2H, aliphatic CH$_2$).

EXAMPLE 7

(2E, 4E)-6-[1-(6-t-butyl-1,1-dimethyl-indan-4-yl)-cyclopropyl]-3-methyl hexadienoic acid (Compound 107)(Structure III, compound 20: R$_2$=t-Bu and R$_8$=R$_9$=Me, prepared as illustrated and described in Scheme 3)

To a solution of 1-(6-t-butyl-1,1-dimethyl-indan-4-yl) ethanone (13) (0.34 g, 1.37 mmol) dissolved in anhydrous CH$_2$Cl$_2$ (15 mL) was added 3-chloro-peroxy benzoic acid (0.40 g, 1.37 mmol) at room temperature. The reaction mixture was allowed to stir overnight during which time the solution changed from clear to cloudy. Added 10 mL of EtOAc and washed organics; first with 5 mL of saturated sodium bicarbonate and then with 5 mL of saturated sodium sulfite. Organic phase was concentrated in vacuo to give a yellow oil in quantitative yield. $^1$H NMR showed that 6-t-butyl-1,1-dimethyl-indan-4-ol acetate (14) was pure enough to carry on to next step without further purification. $^1$H NMR (400 MHz, CDCl$_3$) δ7.03 (d, J=1.6 Hz, 1H, aromatic), 6.86 (d, J=1.7 Hz, 1H, aromatic), 2.71 (t, J=7.2 Hz, 2H, aliphatic CH$_2$), 2.30 (s, 3H, aliphatic CH$_3$), 1.93 (t, J=7.2 Hz, 2H, aliphatic CH$_2$), 1.32 (s, 9H, aliphatic 3CH$_3$).

To a solution of the above indane 14 (0.36 g, 1.37 mmol) dissolved in 15 rnd. MeOH was added solid K$_2$CO$_3$ (0.38 g, 2.74 mmol). The reaction mixture was allowed to stir overnight at room temperature. MeOH was evaporated and the residue was diluted with 10 mL of water. The aqueous layer was then acidified with 5% HCl until pH=4 or 5. Aqueous layer was extracted with EtOAc (2×10 mL). Then the organic layer was washed with saturated NaCl and dried with Na$_2$SO$_4$. Organics were concentrated in vacuo to provide 0.25 g of the 6-t-butyl-1,1-dimethyl-indan-4-ol intermediate in 84% yield that was used directly into the next step. A solution of the above indane (0.25 g, 1.15 mmol) dissolved in 2 mL of dry pyridine was cooled to 0° C.

Trifluoroacetic anhydride (0.36 mL, 2.13 mmol) was slowly added. Resulting mixture was allowed to warm to room temperature and was allowed to stir overnight. Reaction mixture was poured into 15 mL of water and extracted with ether (2×10 mL). Ether extract was sequentially washed with water (10 mL), 10% aq. HCl (2×10 mL), water (10 mL), and saturated NaCl. Organics were then dried with $Na_2SO_4$ and concentrated in vacuo to give 6-t-butyl-1,1-dimethyl-indan-4-ol triflate (15) as a clear oil in 77% yield. $^1$H NMR (400 MHz, CDCl3) δ7.13 (d, J=1.4 Hz, 1H, aromatic), 7.01 (d, J=1.2 Hz, 1H, aromatic), 2.95 (t, J=7.2 Hz, 2H, aliphatic $CH_2$), 1.97 (t, J=7.2 Hz, 2H, aliphatic $CH_2$), 1.31 (s, 9H, aliphatic $3CH_3$) 1.27 (s, 6H, aliphatic $2CH_3$).

The above triflate (15) (310 mg, 0.88 mmol) was coupled with 3-(t-butyldimethylsilyloxybutene) boronic acid as described in Example 1 to give, after desilylation with tetrabutylammonium fluoride in THF, 30 mg of 3-(6-t-butyl-1,1-dimethyl-indan-4-yl)-3-buten-1-ol (16) as a pale yellow oil in 24% yield after column chromatography (10 to 15% EtOAc/hexane). $^1$H NMR (400 MHz, CDCl$_3$) δ7.09 (d, J=1.5 Hz, 1H, aromatic), 7.04 (d, J=1.6 Hz, 1H, aromatic), 5.25 (d, J=1.2 Hz, 1H, vinylic CH), 5.13 (d, J=1.6 Hz, 1H, vinylic CH), 3.68 (q, J=12.2, 6.0 Hz, 2H, aliphatic $CH_2$), 2.84 (t, J=7.2 Hz, 2H, allylic $CH_2$), 2.71 (t, J=6.3 Hz, 2H, aliphatic $CH_2$), 1.89 (t, J=7.2 Hz, 2H, aliphatic $CH_2$), 1.54 (s, 3H, aliphatic $CH_3$), 1.39 (t, J=5.9 Hz, 1H, alcohol), 1.32 (s, 9H, aliphatic $3CH_3$), 1.26 (s, 6H, aliphatic $2CH_3$).

The above unsaturated alcohol (16) (30 mg, 0.16 mmol) was converted to the cyclopropyl alcohol as described in Example 1 to give 33 mg of [1-(6-t-butyl-1,1-dimethyl-indan-4-yl)-cyclopropyl]-ethanol (17) as a pale yellow oil in 67% yield that was used directly for the next step. The above cyclopropyl alcohol (33 mg, 0.15 mmol) was oxidized as described in Example 1 to give 32 mg of 1-(6-t-butyl-1,1-dimethyl-indan-4-yl)-cyclopropaneacetaldehyde (18) as a clear oil in 100% yield. The above cyclopropyl aldehyde 18 (32 mg, 0.15 mmol) and 3-ethoxycarbonyl-2-methylprop-2-enylphosphonate (200 mg, 0.77 mmol) were condensed as described for Example 1 to give 37 mg of ethyl-6-[1-(6-t-butyl-1,1-dimethyl-indan-4-yl)-cyclopropyl]-3-methyl-2,4-hexadienoate (19) as a pale yellow oil in 69% yield.

The above ethyl ester 19 (37 mg, 0.09 mmol) in 2 mL MeOH was hydrolyzed as described for Example 1 to give the crude acid. The crude mixture was purified by HPLC (82% MeOH/18% 10 mmol $NH_4OAc$+0.3% AcOH) to give 18 mg (55%) of pure (2E, 4E)-6-[1-(6-t-butyl-1,1-dimethyl-indan-4-yl)-cyclopropyl]-3-methyl-2,4-hexadienoic acid (20). $^1$H NMR (400 MHz, CDCl$_3$) δ7.05 (d, J=1.5 Hz, 1H, aromatic), 7.02 (d, J=1.7 Hz, 1H, aromatic), 6.09 (dt, J=15.7 and 7.2 Hz, 1H, vinylic CH), 5.97 (d, J=15.7 Hz, 1H, vinylic CH), 5.66 (s, 1H, vinylic CH), 2.90 (t, J=7.2 Hz, 2H, allylic $CH_2$), 2.34 (d, J=7.2 Hz, 2H, allylic $CH_2$), 2.22 (s, 3H, aliphatic $CH_3$), 1.91 (t, J=7.0 Hz, 2H, aliphatic $CH_2$), 1.30 (s, 9H, aliphatic $3CH_3$), 1.25 (s, 6H, aliphatic $2CH_3$), 0.80 (dd, J=10.1, 6.2 Hz, 2H, aliphatic $CH_2$), 0.71 (dd, J=10.2, 3.9 Hz, 2H, aliphatic $CH_2$).

EXAMPLE 8

(2E, 4E)-6-[(5,5,8,8-Tetramethyl-5,6,7,8-tetrahydronaphtha-len-2-yl) cyclopentane-1-yl]-3-methyl hexadienoic acid (Compound 108)(Structure I, compound 26: $R_2$=H, prepared as illustrated and described in Scheme 4).

To a solution of (5,5,8,8-tetramethyl-5,6,7,8-tetrahydronaphthalen-2-yl) bromomethane (21) (100 mg, 0.44 mmol) in acetonitrile (2 mL) was added tetraethylammonium cyanide (83 mg, 0.53 mmol). The resulting golden yellow solution was stirred at rt overnight. The solvent was removed in vacuo and to give a residue that was subjected to chromatograpy (10% EtOAc/90% hexane) to give 59 mg (78%) of (5,5,8,8-tetramethyl-5,6,7,8-tetrahydronaphthalen-2-yl) acetonitrile (22). $^1$H NMR (400 MHz, CDCl$_3$) δ7.31 (d, J=8.2 Hz, 1H, aromatic), 7.23 (d, J=1.8 Hz, 1H, aromatic), 7.08 (dd, J=8.0 and 1.8 Hz, 1H, aromatic), 3.69 (s, 2H, $CH_2$), 1.69 (s, 4H, $2CH_2$), 1.28 (s, 6H, $2CH_3$), (s, 6H, $2CH_3$).

To a mixture of benzonitrile 22 (580 mg, 3.34 mmol) and 1,4-dibromobutane (0.48 mL, 3.34 mmol) in 9 mL of DMF at rt was added portionwise, sodium hydride (400 mg, 10.2 mmol). The reaction mixture was allowed to stir at rt for 2 h after which it was quenched with 15 mL of water and extracted with ethyl acetate (3×20 mL). The organic phase was further washed with brine, dried ($Na_2SO_2$) and concentrated in vacuo to an oil that was subjected to chromatography (5% EtOAc/95% hexane) to give 667 mg (88%) of [(5,5,8,8-tetramethyl-5,6,7,8-tetrahydronaphthalen-2-yl)-cyclopentane-1-yl]acetonitrile that was used directly for the next step. The above nitrile (717 mg, 3.15 mmol) was dissolved in 25 mL of dry dichloromethane and the temperature lowered to −78° C. Then 7.88 mL of DIBAL was added dropwise and the reaction mixture was brought to rt and stirred for 4 h. Quenched with aqueous saturated solution of K, Na tartrate (15 mL) and extracted with dichloromethane (3×20 mL). The organic phase was dried ($Na_2SO_2$) and the solvent was removed in vacuo to give an oil that was subjected to chromatography (5% EtOAc/95% hexane) to give 489 mg (67%) of [(5,5,8,8-tetramethyl-5,6,7,8-tetrahydro-phthalen-2-yl)-cyclopentane-1-yl] formaldehyde (23). $^1$H NMR (400 MHz, CDCl$_3$) δ9.38 (s, 1H, CHO), 7.27 (d, J=8.3 Hz, 1H, aromatic), 7.14 (d, J=2.2 Hz, 1H, aromatic), 7.01 (dd, J=g 8.1 and 2.0 Hz, 1H, aromatic), 2.51 (m, 2H, $CH_2$),1.86 (m, 2H, $CH_2$),1.74 (m, 2H, $CH_2$), 1.67 (s, 4H, $2CH_2$),1.64 (m, 2H, $CH_2$), 1.27 (s, 12H, $4CH_3$).

A solution of (methoxymethyl) triphenyl-phosphonium bromide, mixture with sodium amide (320 mg, 0.72 mmol) in 5 ml of toluene was stirred at rt for 10 min. Then the above aldehyde 23 (149 mg, 0.65 mmol) in 2 mL of toluene was added and the reaction mixture was brought to reflux for 1 h. The reaction was quenched with water (2 mL) and extracted with dichloromethane (2×5 mL). The organic phase was dried ($Na_2SO_2$) and the solvent was removed in vacuo to give an oil that was subjected to chromatography (5% EtOAc/95% hexane) to give 165 mg (86%) of the desired intermediate enol ether that was used directly for the next step. The enol ether was then dissolved in 10 mL of THF and 0.5 mL of concentrated HCl was added. The reaction mixture was allowed to stir at rt for 5 h and then diluted with 10 mL of ethyl acetate. The organic phase was washed with water (4 mL) and dried ($Na_2SO_2$) and the solvent was removed in vacuo to give an oil that was subjected to chromatography (10% EtOAc/90% hexane) to give 108 mg (64%) of 1-(5,5,8,8-tetramethyl-5,6,7,8-tetrahydronaphthalen-2-yl)-cyclopentaneacetaldehyde (24). $^1$H NMR (400 MHz, CDCl$_3$) δ9.41 (t, J=1.4 Hz, 1H, CHO), 7.24 (d, J=8.3 Hz, 1H, aromatic), 7.11 (d, J=2.2 Hz, 1H, aromatic), 7.01 (dd, J=8.1 and 2.0 Hz, 1H, aromatic), 2.53 (d, J=1.4 Hz, 2H, $CH_2$),1.96 (m, 4H, $2CH_2$),1.72 (m, 4H, $2CH_2$), 1.64 (s, 4H, $2CH_2$), 1.25 (s, 12H, $4CH_3$).

The above cyclopentyl aldehyde 24 (108 mg, 0.44 mmol) and 3-ethoxycarbonyl-2-methylprop-2-enylphosphonate (465 mg, 1.76 mmol) were condensed as described for Example 1 to give 63 mg of ethyl-6-[2-(5,5,8,8-tetramethyl-5,6,7,8-tetrahydronaphthalen-2-yl)-cyclopentyl]-3-methyl-2,4-hexadienoate (25) as a pale yellow oil in 58% yield.

The above ethyl ester 25 (63 mg, 0.25 mmol) in 3 mL MeOH was hydrolyzed as described for Example 1 to give the crude acid. The crude mixture was purified by HPLC (87% MeOH/13% 10 mmol $NH_4OAc$+0.3% AcOH) to give 38 mg (65%) of pure (2E, 4E)-6-[2-(5,5,8,8-tetramethyl-5,6,7,8-tetrahydronaphthalen-2-yl)-cyclopentyl]-3-3-methyl-2,4-hexadienoic acid (26). $^1$H NMR (400 MHz, $CDCl_3$) $\delta$7.21 (d, J=8.3 Hz, 1H, aromatic), 7.17 (d, J=1.9 Hz, 1H, aromatic), 7.00 (dd, J=8.2 and 2.0 Hz, 1H, aromatic), 6.27 (dt, J=15.9 and 6.8 Hz, 1H, olefinic CH), 6.00 (d, J=15.9 Hz, 1H, olefinic CH), 5.78 (s, 1H, olefinic CH), 2.39 (d, J=6.8 Hz, 2H, $CH_2$), 2.25 (s, 3H, $CH_3$), 2.03 (m, 4H, $2CH_2$), 1.71 (m, 4H, $2CH_2$), 1.67 (s, 4H, $2CH_2$), 1.27 (s, 6H, $2CH_3$), 1.26 (s, 6H, $2CH_3$).

Evaluation of Retinoid Receptor Subfamily Activity

Utilizing the "cis-trans" or "co-transfection" assay described by Evans et al., *Science*, 240:889–95 (May 13, 1988), the disclosure of which is herein incorporated by reference, the retinoid compounds of the present invention were tested and found to have strong, specific activity as either selective RXR agonists, or as pan-agonist activators of both RAR and RXR receptors. This assay is described in further detail in U.S. Pat. Nos. 4,981,784 and 5,071,773, the disclosures of which are incorporated herein by reference.

The co-transfection assay provides a method for identifying functional agonists which mimic, or antagonists which inhibit, the effect of native hormones, and quantifying their activity for responsive IR proteins. In this regard, the co-transfection assay mimics an in vivo system in the laboratory. Importantly, activity in the co-transfection assay correlates very well with known in vivo activity, such that the co-transfection assay functions as a qualitative and quantitative predictor of a tested compounds in vivo pharmacology. See, e.g., T. Berger et al. 41 *J. Steroid Biochem. Molec. Biol.* 773 (1992), the disclosure of which is herein incorporated by reference.

In the co-transfection assay, a cloned cDNA for an IR (e.g., human RARα, RARβ, RXRγ) under the control of a constitutive promoter (e.g., the SV 40 promoter) is introduced by transfection (a procedure to induce cells to take up foreign genes) into a background cell substantially devoid of endogenous IRs. This introduced gene directs the recipient cells to make the IR protein of interest. A second gene is also introduced (co-transfected) into the same cells in conjunction with the IR gene. This second gene, comprising the cDNA for a reporter protein, such as firefly luciferase (LUC), controlled by an appropriate hormone responsive promoter containing a hormone response element (HRE). This reporter plasmid functions as a reporter for the transcription-modulating activity of the target IR. Thus, the reporter acts as a surrogate for the products (mRNA then protein) normally expressed by a gene under control of the target receptor and its native hormone.

The co-transfection assay can detect small molecule agonists or antagonists of target IRs. Exposing the transfected cells to an agonist ligand compound increases reporter activity in the transfected cells. This activity can be conveniently measured, e.g., by increasing luciferase production, which reflects compound-dependent, IR-mediated increases in reporter transcription. To detect antagonists, the co-transfection assay is carried out in the presence of a constant concentration of an agonist to the target IR (e.g., all-trans retinoic acid for RARα) known to induce a defined reporter signal. Increasing concentrations of a suspected antagonist will decrease the reporter signal (e.g., luciferase production). The co-transfection assay is therefore useful to detect both agonists and antagonists of specific IRs. Furthermore, it determines not only whether a compound interacts with a particular IR, but whether this interaction mimics (agonizes) or blocks (antagonizes) the effects of the native regulatory molecules on target gene expression, as well as the specificity and strength of this interaction.

The activity of the retinoid compounds of the present invention were evaluated utilizing the co-transfection assay according to the following illustrative Example.

EXAMPLE 9
Co-transfection Assay

CV-1 cells (African green monkey kidney fibroblasts) were cultured in the presence of Dulbecco's Modified Eagle Medium (DMEM) supplemented with 10% charcoal resin-stripped fetal bovine serum then transferred to 96-well microtiter plates one day prior to transfection.

To determine RAR and/or RXR agonist activity of the compounds of the present invention, the CV-1 cells were transiently transfected by calcium phosphate coprecipitation according to the procedure of Berger et al., 41 *J. Steroid Biochem. Mol. Biol.*, 733 (1992) with the following receptor expressing plasmids: pRShRARα: Giguere et al., 330 *Nature*, 624 (1987); pRShRARβ and pRShRARγ, Ishikawa et al., 4 *Mol. Endocrin.*, 837 (1990); pRShRXRα, Mangelsdorf et al., 345 *Nature*, 224 (1990); and pRSmRXRβ and pRSmRXRγ, Mangelsdorf et al., 6 *Genes & Devel.*, 329 (1992), the disclosures of which are herein incorporated by reference. Each of these receptor expressing plasmids was co-transfected at a concentration of 5 ng/well, along with a basal reporter plasmid at 100 ng/well, the internal control plasmid pRS-β-Gal at 50 ng/well and filler DNA, pGEM at 45 ng/well.

The basal reporter plasmid D-MTV-LUC (Hollenberg and Evans, 55 *Cell*, 899 (1988), the disclosure of which is herein incorporated by reference) containing two copies of the TRE-palindromic response element described in Umesono et al., 336 *Nature*, 262 (1988), the disclosure of which is herein incorporated by reference, was used in transfections for the RARs, and the reporter plasmid CRBPIIFKLUC, which contains an RXRE (retinoid X receptor response element, as described in Mangelsdorf et al., 66 *Cell*, 555 (1991), the disclosure of which is herein incorporated by reference), was used in transfections for the RXRs. Each of these reporter plasmids contains the cDNA for firefly luciferase (LUC) under constitutive promoter containing the appropriate RAR or RXR response element. As noted above, pRS-β-Gal, coding for constitutive expression of E. coli β-galactosidase (β-Gal), was included as an internal control for evaluation of transfection efficiency and compound toxicity.

Six hours after transfection, media was removed and the cells were washed with phosphate-buffered saline (PBS). Media containing compounds of the present invention in concentrations ranging from $10^{-12}$ to $10^{-5}$ M were added to the cells. Similarly, the reference compounds all-trans retinoic acid (ATRA)(Sigma Chemical), a known RAR selective compound, and 9-cis retinoic acid (9-cis) (synthesized as described in Heyman et al., *Cell*, 68:397–406 (1992)), a compound with known activity on RXRs, were added at similar concentrations to provide a reference point for analysis of the activity of the compounds of the present invention. Retinoid purity was established as greater than 99% by reverse phase high-performance liquid chromatography. Retinoids were dissolved in dimethylsulfoxide for use in the transcriptional activation assays. Three to four replicates were used for each sample.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

LUC response/β-Gal rate where β-Gal rate=β-Gal·1×10$^{-5}$/β-Gal incubation time.

The mean and standard error of the mean (SEM) of the NR were calculated. Data was plotted as the response of the compound compared to the reference compounds over the range of the dose-response curve. For the agonist compounds of the present invention, the effective concentration that produced 50% of the maximum response (EC$_{50}$) was quantified.

The potency (nM) of selected retinoid compounds of the present invention are in Table 1 below.

TABLE 1

Potency (nM) of selected retinoid compounds of the present invention on RARα,β,γ and RXRα,β,γ, in comparison to the known RAR-active retinoid compound all-trans retinoic acid (ATRA) and RXR-active retinoid compound 9-cis retinoic acid (9-cis-RA).

| Cmpd. No. | RARα Pot nM | RARβ Pot nM | RARγ Pot nM | RXRα Pot nM | RXRβ Pot nM | RXRγ Pot nM |
|---|---|---|---|---|---|---|
| 101 | 59 | 17 | 24 | 13 | 6 | 14 |
| 102 | na | na | na | 31 | 9 | 36 |
| 105 | 733 | 139 | 391 | 30 | 19 | 23 |
| 107 | na | na | na | 34 | 22 | 20 |
| 108 | na | na | na | 63 | nt | 66 |
| ATRA | 436 | 78 | 19 | 1015 | 1211 | 961 |
| 9-cis | 220 | 29 | 50 | 195 | 128 | 124 | na = not active (potency of >10,000 and/or efficacy of ≦20%);
nt = not tested

As can been seen in Table 1, Compounds 102, 107 and 108 are extremely potent RXR selective compounds. In fact, these Compounds showed no activity at all for the RAR receptors. In addition, Compounds 101 and 105 are pan-agonists that display superior potency profiles to that of the known pan-agonist compound 9-cis retinoic acid.

EXAMPLE 10

In addition to the cotransfection data of Example 9, the binding of selected compounds of the present invention to the RAR and RXR receptors was also investigated according to the methodology described in M. F., Boehm, et al., "Synthesis and Structure-Activity Relationships of Novel Retinoid X Receptor Selective Retinoids", 37 *J. Med. Chem.*, 2930 (1994); M. F. Boehm, et al., "Synthesis of High Specific Activity [$^3$H-]-9-cis Retinoic Acid and Its Application for Identifying Retinoids with Unusual Binding Properties", 37 *J. Med. Chem.*, 408 (1994), and E. A. Allegretto, et al., "Characterization and Comparison of Hormone-Binding and Transactivation Properties of Retinoic Acid and Retinoid X Receptors Expressed in Mammalian Cells and Yeast", 268 *J. Biol. Chem.*, 22625 (1993), the disclosures of which are herein incorporated by reference.

Non-specific binding was defined as that binding remaining in the presence of 500 nM of the appropriate unlabelled compound. At the end of the incubation period, bound from free ligand were separated. The amount of bound tritiated retinoids was determined by liquid scintillation counting of an aliquot (700 mL) of the supernatant fluid or the hydroxylapatite pellet.

After correcting for non-specific binding, IC$_{50}$ values were determined. The IC$_{50}$ value is defined as the concentration of competing ligand needed to reduce specific binding by 50%. The IC$_{50}$ value was determined graphically from a log-logit plot of the data. The K$_i$ values were determined by application of the Cheng-Prussof equation to the IC$_{50}$ values, the labeled ligand concentration and the K$_d$ of the labeled ligand.

The binding activity (Kd in nM) results of selected retinoid compounds of present invention, and the reference compounds ATRA, and 9-cis RA, is shown in Table 2 below.

TABLE 2

Binding (Kd in nM) of selected retinoid compounds of the present invention on RARα,β,γ and RXRα,β,γ proteins in comparison to the known RAR-active retinoid compound all-trans retinoic acid (ATRA) and RXR-active retinoid compound 9-cis retinoic acid (9-cis-RA).

| Cmpd. No. | RARα Binding Kd (nM) | RARβ Binding Kd (nM) | RARγ Binding Kd (nM) | RXRα Binding Kd (nM) | RXRβ Binding Kd (nM) | RXRγ Binding Kd (nM) |
|---|---|---|---|---|---|---|
| 101 | 644 | 463 | 552 | 2 | 6 | 8 |
| 102 | na | na | na | 16 | 18 | 153 |
| 105 | na | na | na | 3 | 8 | 16 |
| 107 | na | na | na | 6 | 15 | 22 |
| 108 | na | na | na | 41 | 357 | 128 |
| ATRA | 15 | 17 | 17 | 53 | 306 | 306 |
| 9-cis | 93 | 97 | 148 | 8 | 15 | 14 | na = not active (Kd of >5,000)

As can be seen in Table 2, the compounds of the present invention show comparable binding to the known RAR active compound ATRA, and the known RXR active compound 9-cis retinoic acid.

EXAMPLE 11

The in vitro affect of Compound 101 of the present invention on the recognized cancer cell lines, RPMI 8226, ME 180 and AML-193, obtained from the American Type Culture Collection (ATCC, Rockville, Md.), was investigated.

RPMI 8226 is a human hematopoietic cell line obtained from the peripheral blood of a patient with multiple myeloma, and as such is a recognized model for multiple myelomas and related malignancies. Y. Matsuoka, G. E. Moore, Y. Yagi and D. Pressman, "Production of free light chains of immunoglobulin by a hematopoietic cell line derived from a patient with multiple myeloma", 125 *Proc. Soc. Exp. Biol. Med.*, 1246 (1967), the disclosure of which is herein incorporated by reference. The cells resemble the lymphoblastoid cells of other human lymphocyte cell lines and secretes λ-type light chains of immunoglobulin. RPMI 8226 cells were grown in RPMI medium (Gibco) supplemented with 10% fetal bovine serum, glutamine and antibiotics. The cells were maintained as suspension cultures grown at 37° C. in a humidified atmosphere of 5% CO$_2$ in air. The cells were diluted to a concentration of 1×10$^5$/mL twice a week.

ME 180 is a human epidermoid carcinoma cell line derived from the cervix, and as such is a recognized model for squamous cell carcinomas and related malignancies. J. A. Sykes, J. Whitescarver, P. Jermstrom, J. F. Nolan and P. Byatt, "Some properties of a new epithelial cell line of human origin", 45 *MH-Adenoviridae J. Natl. Cancer Inst.*, 107 (1970), the disclosure of which is herein incorporated by reference. The tumor was a highly invasive squamous cell carcinoma with irregular cell clusters and no significant keratinization. ME 180 cells were grown and maintained in McCoy's 5a medium (Gibco) supplemented with 10% fetal bovine serum, glutamine and antibiotics. The cells were maintained as monolayer cultures grown at 37° C. in a humidified atmosphere of 5% $CO_2$ in air.

The AML-193 cell line was established from the blast cells of a patient with leukemia and was classified as M5 Acute Monocytic Leukemia, and as such is a recognized model for leukemias and related malignancies. G. Rovera, et al., 139 *J. Immunol.*, 3348 (1987), the disclosure of which is herein incorporated by reference. Over 75% of these cells are positive by immunofluorescence for the myelomonocytic antigen CS15. The cells were grown in Iscove's modified Dulbeccos's medium with 5 μg/mL transferring, 5 μg/mL insulin and 2 ng/mL rh GM-CSF. The cells were maintained as suspension cultures grown at 37° C. in a humidified atmosphere of 5% $CO_2$ in air. The cells were diluted to a concentration of $1\times10^5$/mL twice a week.

Incorporation of $^3$H-Thymidine

Measurement of the level of radiolabeled thymidine incorporated into the above-identified cell lines provides a direct measurement of the antiproliferative properties of the compounds of the present invention. The method used for determination of the incorporation of radiolabeled thymidine was adapted from the procedure described by S. Shrivastav et al., "An in vitro assay procedure to test chemotherapeutic drugs on cells from human solid tumors", 40 *Cancer Res.*, 4438 (1980), the disclosure of which is herein incorporated by reference. RPMI 8226 or AML-193 cells were plated in a 96 well round bottom microtiter plate (Costar) at a density of 1,000 cells/well. To appropriate wells, retinoid test compounds were added at the final concentrations indicated for a final volume of 150 μL/well. The plates were incubated for 96 hours at 37° C. in a humidified atmosphere of 5% $CO_2$ in air. Subsequently, 1 μCi of [5'-$^3$H]-thymidine (Amersham, U.K, 43 Ci/mmol specific activity) in 25 μL culture medium was added to each well and the cells were incubated for an additional six hours. The cultures were further processed as described below.

ME 180 cells, harvested by trypsinization were plated in a 96 well flat bottom microtiter plate (Costar) at a density of 2,000 cells/well. The cultures were treated as described above for RPMI 8226 with the following exceptions. After incubation, the supernatant was carefully removed, and the cells were washed with a 0.5 mM solution of thymidine in phosphate buffered saline. ME 180 cells were briefly treated with 50 μL of 2.5% trypsin to dislodge the cells from the plate. Both cell lines were then processed as follows: the cellular DNA was precipitated with 10% trichloroacetic acid onto glass fiber filter mats using a SKATRON multi-well cell harvester (Skatron Instruments, Sterling Va.). Radioactivity incorporated into DNA, as a direct measurement of cell growth, was measured by liquid scintillation counting. The mean disintegrations per minute of incorporated thymidine from triplicate wells was determined. The $IC_{50}$ (nM concentration required to inhibit 50% of the maximally observed incorporation of thymidine) for Compound 101 of the present invention, and reference compounds ATRA, TTNBP and 9-cis-RA are shown below in Table 4 for the cell lines RPMI 8226, ME 180 and AML-193.

Table 4: Inhibitory concentration required to inhibit 50% of the maximally observed radiolabeled thymidine (TdR $IC_{50}$) in nM for Compound 101 of the present invention and reference compounds ATRA, TTNBP and 9-cis-RA on the RPMI 8226, ME 180 and AML-193 cell lines.

| Compound | TdR $IC_{50}$ RPMI 8226 (nM) | TdR $IC_{50}$ ME 180 (nM) | TdR $IC_{50}$ AML-193 (nM) |
| --- | --- | --- | --- |
| 101 | <0.1 | 0.9 | <0.1 |
| ATRA | 102 | 253 | 197 |
| TTNPB | 0.2 | 0.4 | 0.1 |
| 9-cis-RA | 150 | 180 | 113 |

EXAMPLE 12

The following examples provide illustrative pharmacological composition formulations. Hard gelatin capsules are prepared using the following ingredients:

|  | Quantity (mg/capsule) |
| --- | --- |
| Compound 101b | 140 |
| Starch, dried | 100 |
| Magnesium stearate | 10 |
| Total | 250 mg |

The above ingredients are mixed and filled into hard gelatin capsules in 250 mg quantities.

A tablet is prepared using the ingredients below:

|  | Quantity (mg/tablet) |
| --- | --- |
| Compound 101b | 140 |
| Cellulose, microcrystalline | 200 |
| Silicon dioxide, fumed | 10 |
| Stearic acid | 10 |
| Total | 360 mg |

The components are blended and compressed to form tablets each weighing 360 mg. Tablets, each containing 60 mg of active ingredient, are made as follows:

|  | Quantity (mg/tablet) |
| --- | --- |
| Compound 101b | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. And passed through a No. 18 mesh U.S. sieve. The SCMS, magnesium stearate, and talc, previously passed through a No. 60 mesh U.S. sieve, are then added to the granules which, after mixing, are compressed on a tablet machine to yield tablets each weighing 150 mg.

Suppositories, each containing 225 mg of active ingredient, may be made as follows:

| | |
|---|---|
| Compound 101b | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:

| | |
|---|---|
| Compound 101b | 100 mg |
| Isotonic saline | 1,000 ml |
| Glycerol | 100 ml |

The compound is dissolved in the glycerol and then the solution is slowly diluted with isotonic saline. The solution of the above ingredients is then administered intravenously at a rate of 1 ml per minute to a patient.

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A compound of the formula:

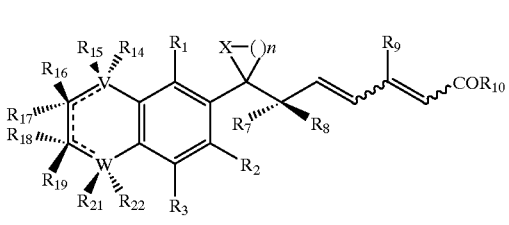
(I)

OR

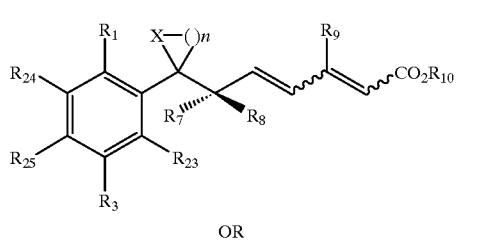
(II)

OR

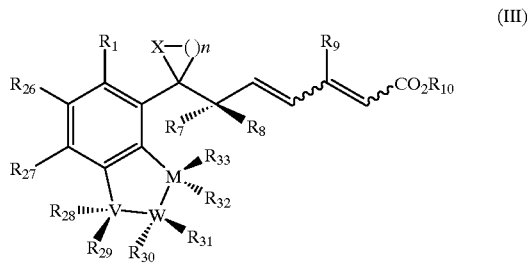
(III)

wherein, $R_1$ is hydrogen or a $C_1$–$C_{10}$ alkyl, F or $OR_4$, where $R_4$ has the definition given below;

$R_2$ is hydrogen, $CH_3$, $OCH_3$ or $NO_2$;

$R_3$ is hydrogen, F, a $C_1$–$C_{12}$ alkyl, $CF_3$, $NO_2$, $OR_4$ or $NR_5R_6$, where $R_4$ is hydrogen, a $C_1$–$C_6$ alkyl or $C_7$–$C_{15}$ arylalkyl, and where $R_5$ and $R_6$ each independently are hydrogen, a $C_1$–$C_6$ alkyl, $C_7$–$C_{15}$ arylalkyl, aryl, ortho-, meta-, or para-substituted hydroxyalkyl or taken together are a $C_3$–$C_6$ cycloalkyl, provided that $R_5$ must be a hydrogen when $R_6$ is aryl or hydroxyaryl;

$R_7$ and $R_8$ each independently are hydrogen or a $C_1$–$C_6$ alkyl;

$R_9$ is hydrogen or a $C_1$–$C_6$ alkyl or $CF_3$;

$R_{10}$ is $OR_{11}$ or $NR_{12}R_{13}$, where $R_{11}$ is hydrogen, a $C_1$–$C_6$ alkyl, with $R_{12}$ and $R_{13}$ each independently being hydrogen, a $C_1$–$C_6$ alkyl, aryl or ortho-, meta- and para-substituted hydroxy aryl;

$R_{14}$–$R_{15}$ each independently are hydrogen, a $C_1$–$C_{12}$ alkyl, $C_7$–$C_{15}$ arylalkyl or $CF_3$;

$R_{16}$–$R_{19}$ each independently are hydrogen, a $C_1$–$C_{12}$ alkyl, $C_7$–$C_{15}$ arylalkyl, $CF_3$, $OR_{20}$ or $NR_5R_6$, where $R_{20}$ is hydrogen, benzyl, a $C_1$–$C_{10}$ alkyl or a $C_7$–$C_{15}$ arylalkyl, and where $R_5$ and $R_6$ have the definitions given above, or $R_{16}$–$R_{19}$ taken together are keto or $R_{16}$ and $R_{17}$, $R_{18}$ and $R_{19}$, $R_{16}$ and $R_{19}$, $R_{17}$ and $R_{18}$ are epoxy or cyclopropyl;

$R_{21}$ and $R_{22}$ each independently are hydrogen, a $C_1$–$C_6$ alkyl or a $C_7$–$C_{15}$ arylalkyl;

$R_{23}$ is hydrogen, $NO_2$, a $C_1$–$C_3$ alkyl, OH, $OCH_3$ or $OC_2H_5$;

$R_{24}$–$R_{27}$ each independently are hydrogen, a $C_1$–$C_{12}$ alkyl, $C_7$–$C_{15}$ arylalkyl, $CF_3$, $OR_{20}$ or $NR_5R_6$, where $R_5$, $R_6$ and $R_{20}$ have the definitions given above;

$R_{28}$–$R_{33}$ each independently are hydrogen, a $C_1$–$C_{12}$ alkyl, $C_7$–$C_{15}$ arylalkyl or $CF_3$;

V, M and W independently represent C, O, S, N, SO or $SO_2$, provided, however, that when V or M or W are O, S, SO and $SO_2$, then $R_{14}$ and $R_{15}$ or $R_{16}$ and $R_{17}$ or $R_{18}$ and $R_{19}$ or $R_{21}$ and $R_{22}$ in structures I and III respectively do not exist, and further provided, that when V or M or W is N, then one each of $R_{14}$ and $R_{15}$ or $R_{16}$ and $R_{17}$ or $R_{18}$ and $R_{19}$ or $R_{21}$ and $R_{22}$ in structures I and III respectively, do not exist;

X represents C, O, N or $CF_2$;

n=1, 2, 3 or 4;

the dotted lines in structures I and III represent optional double bonds; and the wavy lines represent olefin bonds that are either in the cis (Z) or trans (E) configuration, provided, however, that the double bonds cannot be contiguous, and further provided that when such optional double bonds exist then the substitution patterns around such bonds cannot violate double bond valency.

2. A compound according to claim 1, selected from the group consisting of (2E, 4E)-6-[1-(5,5,8,8-Tetramethyl-5,6,7,8-tetrahydronaphtha-len-2-yl) cyclopropanyl]-3-methyl hexadienoic acid (Compound 101); (2E, 4E)-6-[(3,5,5,8,8-Pentamethyl-5,6,7,8-tetrahydronaphthalen-2-yl) cyclopropan-1-yl]-3-methyl hexadienoic acid (Compound 102); (2E, 4E)-6-[(5,5,8,8-Tetramethyl-3-methoxy-5,6,7,8-tetrahydronaphtha-len-2-yl) cyclopropan-1-yl]-3-methyl hexadienoic acid (Compound 103); (2E, 4E)-6-[(3,5-di-t-butyl phenyl) cyclopropan-1-yl]-3-methyl hexadienoic acid (Compound 105); (2E, 4E)-6-[(3,4-diethyl phenyl) cyclopropan-1-yl]-3-methyl hexadienoic acid (Compound 106); (2E, 4E)-6-[1-(6-t-butyl-1,1-dimethyl-indan-4-yl)- cyclopropyl]-3-methyl hexadienoic acid (Compound 107); and (2E, 4E)-6-[(5,5,8,8-Tetramethyl-5,6,7,8-tetrahydronaphtha-len-2-yl) cyclopentane-1-yl]-3-methyl hexadienoic acid (Compound 108).

3. A compound according to claim 1, wherein the compound exhibits retinoid receptor agonist activity.

4. A compound according to claim 3, wherein the compound exhibits 50% maximal activation of one or more retinoid receptors at a concentration of less than 100 nM.

5. A compound according to claim 3, wherein the compound exhibits 50% maximal activation of one or more retinoid receptors at a concentration of less than 50 nM.

6. A compound according to claim 3, wherein the compound exhibits 50% maximal activation of one or more retinoid receptors at a concentration of less than 20 nM.

7. A compound according to claim 3, wherein the compound exhibits 50% maximal activation of one or more retinoid receptors at a concentration of less than 10 nM.

8. A compound according to claim 3, wherein the compound exhibits activity as a selective RXR agonist.

9. A compound according to claim 8, wherein the compound is at least two times more potent an activator of RXR than of RAR.

10. A compound according to claim 8, wherein the compound is at least five times more potent an activator of RXR than of RAR.

11. A compound according to claim 8, wherein the compound is at least ten times more potent an activator of RXR than of RAR.

12. A compound according to claim 8, wherein the compound is at least one hundred times more potent an activator of RXR than of RAR.

13. A compound according to claim 3, wherein the compound exhibits activity as both an activator of RAR and RXR.

14. A compound according to claim 1, wherein the compound is administered to a patient as a dosage unit at from about 1 µg/kg of body weight to about 500 mg/kg of body weight.

15. A compound according to claim 1, wherein the compound is administered to a patient as a dosage unit at from about 10 µg/kg of body weight to about 250 mg/kg of body weight.

16. A compound according to claim 1, wherein the compound is administered to a patient as a dosage unit at from about 20 µg/kg of body weight to about 100 mg/kg of body weight.

17. A compound according to claim 3, wherein the compound is effective in treating skin-related diseases and conditions, cancerous and pre-cancerous conditions, diseases of the eye, cardiovascular diseases, inflammatory diseases, neurodegenerative diseases, diseases involving modulation of apoptosis, diseases of the immune system, improper pituitary function, diseases involving human papilloma virus, wound healing or restoration of hair growth.

18. A pharmaceutical composition comprising a compound of claim 1 and a pharmaceutically acceptable carrier.

19. A pharmaceutical composition according to claim 18, wherein the composition is formulated for oral, topical, intravenous, suppository or parental administration.

20. A pharmaceutical composition according to claim 18, wherein the compound is administered to a patient as a dosage unit at from about 1 µg/kg of body weight to about 500 mg/kg of body weight.

21. A pharmaceutical composition according to claim 18, wherein the compound is administered to a patient as a dosage unit at from about 10 µg/kg of body weight to about 250 mg/kg of body weight.

22. A pharmaceutical composition according to claim 18, wherein the compound is administered to a patient as a dosage unit at from about 20 µg/kg of body weight to about 100 mg/kg of body weight.

23. A pharmaceutical composition according to claim 18, wherein the composition is effective in treating skin-related diseases and conditions, cancerous and pre-cancerous conditions, diseases of the eye, cardiovascular diseases, inflammatory diseases, neurodegenerative diseases, diseases involving modulation of apoptosis, diseases of the immune system, improper pituitary function, diseases involving human papilloma virus, wound healing or restoration of hair growth.

24. A pharmaceutical composition according to claim 18, wherein the composition exhibits activity as a selective RXR agonist.

25. A pharmaceutical composition according to claim 18, wherein the composition exhibits activity as both an activator of RAR and RXR.

26. A method of affecting RAR and/or RXR activity comprising the in vivo administration of a compound according to claim 3.

27. A method of modulating processes mediated by RAR and/or RXR receptors comprising administering to a patient an amount of a compound according to claim 3, said amount being effective to modulate one or more processed mediated by RAR and/or RXR receptors.

28. A method of treating a patient requiring retinoid therapy comprising administering to the patient a pharmaceutically effective amount of a compound according to claim 3.

29. A method of treating a patient according to claim 28, wherein the compound is effective in treating skin-related diseases and conditions, cancerous and pre-cancerous conditions, diseases of the eye, cardiovascular diseases, inflammatory diseases, neurodegenerative diseases, diseases involving modulation of apoptosis, diseases of the immune system, improper pituitary function, diseases involving human papilloma virus, wound healing or restoration of hair growth.

30. A method of treating a patient requiring retinoid therapy comprising administering to the patient a pharmaceutically effective amount of a pharmaceutical composition according to claim 18.

31. A method of treating a patient according to claim 30, wherein the composition is effective in treating skin-related diseases and conditions, cancerous and pre-cancerous conditions, diseases of the eye, cardiovascular diseases, inflammatory diseases, neurodegenerative diseases, diseases involving modulation of apoptosis, diseases of the immune system, improper pituitary function, diseases involving human papilloma virus, wound healing or restoration of hair growth.

32. A compound of the formula:

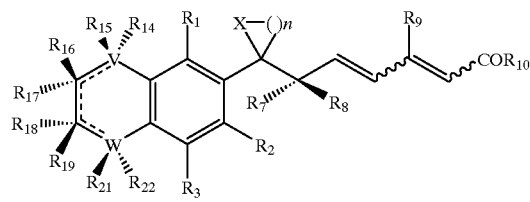

wherein,
$R_1$ and $R_3$ each independently are hydrogen or a $C_1$–$C_{10}$ alkyl, F or $OR_4$ where $R_4$ is hydrogen, a $C_1$–$C_6$ alkyl or $C_7$–$C_{15}$ arylalkyl;

$R_2$ is hydrogen, $NO_2$, $CH_3$ or $OCH_3$;

$R_7$ and $R_8$ each independently are hydrogen or a $C_1$–$C_6$ alkyl;

$R_9$ is hydrogen or a $C_1$–$C_6$ alkyl or $CF_3$;

$R_{10}$ is $OR_{11}$ or $NR_{12}R_{13}$, where $R_{11}$ is hydrogen, a $C_1$–$C_6$ alkyl, and with $R_{12}$ and $R_{13}$ each independently being hydrogen, a $C_1$–$C_6$ alkyl, aryl or ortho-, meta- and para-substituted hydroxy aryl;

$R_{14}$, $R_{15}$, $R_{21}$ and $R_{22}$ each independently are hydrogen, a $C_1$–$C_6$ alkyl or a $C_7$–$C_{15}$ arylalkyl;

$R_{16}$ through $R_{19}$ each independently are hydrogen, a $C_1$–$C_2$ alkyl or $OR_{23}$, where $R_{23}$ is hydrogen or a $C_1$–$C_{10}$ alkyl, or $R_{16}$–$R_{19}$ taken together are keto or $R_{16}$ and $R_{17}$, $R_{18}$ and $R_{19}$, $R_{16}$ and $R_{19}$, $R_{17}$ and $R_{18}$ are epoxy or cyclopropyl;

V and W independently represent C, O, S, N, SO or $SO_2$, provided, however, that when V or W are O, S, SO and $SO_2$, then either $R_{14}$ and $R_{15}$ or $R_{21}$ and $R_{22}$ respectively do not exist, and further provided, that when V or W is N, then one each of $R_{14}$ and $R_{15}$ or $R_{21}$ and $R_{22}$ respectively, do not exist;

X represents C, O, N or $CF_2$;

n=1, 2, 3 or 4;

the dotted lines in structures I and III represent optional double bonds; and the wavy lines represent olefin bonds that are either in the cis (Z) or trans (E) configuration, provided, however, that the double bonds cannot be contiguous, and further provided that when such optional double bonds exist then the substitution patterns around such bonds cannot violate double bond valency.

33. A compound of the formula:

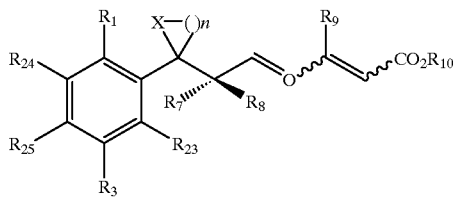

wherein, $R_1$ is hydrogen or a $C_1$–$C_{10}$ alkyl;

$R_3$ and $R_{24}$ each independently are hydrogen, a $C_1$–$C_6$ alkyl, branched alkyl, $CF_3$ or $NR_{24}R_{25}$, where $R_{24}$ and $R_{25}$ are $C_1$–$C_4$ alkyls;

$R_7$ and $R_8$ are hydrogen or a $C_1$–$C_6$ alkyl;

$R_9$ is a hydrogen or a $C_1$–$C_6$ alkyl or $CF_3$;

$R_{10}$ is $OR_{11}$ or $NR_{12}R_{13}$, where $R_{11}$ is hydrogen, a $C_1$–$C_6$ alkyl, and with $R_{12}$ and $R_{13}$ each independently being hydrogen, a $C_1$–$C_6$ alkyl, aryl or ortho-, meta- and para-substituted hydroxy aryl;

$R_{23}$ is hydrogen, $NO_2$, a $C_1$–$C_3$ alkyl, OH, $OCH_3$ or $OC_2H_5$;

$R_{25}$ is hydrogen, $C_1$–$C_8$ alkyl and $OR_{26}$ with $R_{26}$ being a $C_1$–$C_7$ alkyl or benzyl;

X represents C, O, N of $CF_2$;

n=1, 2, 3 or 4; and the wavy lines represent olefin bonds that are either in the cis (Z) or trans (E) configuration, provided, however, that the double bonds cannot be contiguous, and further provided that when such optional double bonds exist then the substitution patterns around such bonds cannot violate double bond valency.

34. A compound of the formula:

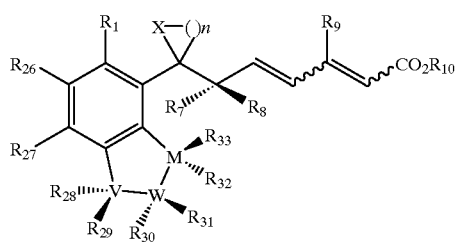

wherein, $R_1$ is hydrogen;

$R_{26}$–$R_{27}$ each independently are hydrogen, a $C_1$–$C_{12}$ alkyl, $C_7$–$C_{15}$ arylalkyl, $CF_3$, $OR_{20}$ or $NR_5R_6$, where $R_5$ and $R_6$ each independently are hydrogen, a $C_1$–$C_6$ alkyl, $C_7$–$C_{15}$ arylalkyl, aryl, ortho-, meta-, or para-substituted hydroxyalkyl or taken together are a $C_3$–$C_6$ cycloalkyl, provided that $R_5$ must be a hydrogen when $R_6$ is aryl or hydroxyaryl, and where $R_{20}$ is hydrogen, benzyl, a $C_1$–$C_{10}$ alkyl or a $C_7$–$C_{15}$ arylalkyl;

$R_{28}$–$R_{33}$ each independently are hydrogen, a $C_1$–$C_{12}$ alkyl, $C_7$–$C_{15}$ arylalkyl or $CF_3$;

$R_7$ and $R_8$ each independently are hydrogen or a $C_1$–$C_6$ alkyl;

$R_9$ is a hydrogen or a $C_1$–$C_6$ alkyl or $CF_3$;

$R_{10}$ is $OR_{11}$ or $NR_{12}R_{13}$, where $R_{11}$ is hydrogen, a $C_1$–$C_6$ alkyl, and with $R_{12}$ and $R_{13}$ each independently being hydrogen, a $C_1$–$C_6$ alkyl, aryl or ortho-, meta- and para-substituted hydroxyaryl;

M, W and V each independently represent C, O or N;

X represents C, O, N or $CF_2$;

n=1, 2, 3 or 4;

the dotted lines represent optional double bonds; and the wavy lines represent olefin bonds that are either in the cis (Z) or trans (E) configuration, provided, however, that the double bonds cannot be contiguous, and further provided that when such optional double bonds exist then the substitution patterns around such bonds cannot violate double bond valency.

* * * * *